United States Patent [19]
Chang

[11] Patent Number: 5,567,620
[45] Date of Patent: Oct. 22, 1996

[54] NON-DENATURING POTENCY ASSAY FOR SOMATOTROPIN

[75] Inventor: Jen P. Chang, Indianapolis, Ind.

[73] Assignee: Eli Lilly and Company, Indianapolis, Ind.

[21] Appl. No.: 468,015

[22] Filed: Jun. 6, 1995

Related U.S. Application Data

[63] Continuation-in-part of Ser. No. 357,073, Dec. 15, 1994, abandoned, which is a continuation of Ser. No. 9,034, Jan. 26, 1993, abandoned.

[51] Int. Cl.$^6$ .................................................. G01N 30/06
[52] U.S. Cl. ........................ 436/87; 436/161; 436/174; 530/399; 530/417
[58] Field of Search ............................... 436/86, 87, 161, 436/175, 177, 178, 817; 210/635, 639; 530/399, 417

[56] References Cited

U.S. PATENT DOCUMENTS

| | | | |
|---|---|---|---|
| 4,977,140 | 12/1990 | Ferguson et al. | 530/399 X |
| 5,064,943 | 11/1991 | McCoy et al. | 530/399 |
| 5,079,230 | 1/1992 | Randawa et al. | 530/399 X |
| 5,151,501 | 9/1992 | McCoy | 530/403 X |

OTHER PUBLICATIONS

Seaman, W. J. et al., "The lack of a growth-promoting effect of orally administered bovine somatotropin in the rat body-weight gain bioassay", Chemical Abstracts, vol. 108, No. 13, 106843r (1988).

Riggin, R. M. et al., " High–Performance Size–Exclusion Chromatographic Determination of the Potency of Biosynthetic Human Growth Hormone Products", Journal of Chromatography, vol. 435, 307–318 (1988).

Andersson, T. et al., "Agarose–Based Media for High–Resolution Gel Filtration of Biopolymers", Journal of Chromatography, vol. 326, 33– 44 (1985).

*Primary Examiner*—Jeffrey Snay
*Attorney, Agent, or Firm*—Woodard, Emhardt, Naughton, Moriarty & McNett

[57] ABSTRACT

Described are methods for determining the potency of somatotropins. The level of biologically active bovine somatotropin protein in a bovine somatotropin sample is measured by size exclusion HPLC employing as the stationary phase a hydrophilic porous gel having an average particle diameter of about 5 μm to about 15 μm and the a mobile phase a buffered aqueous solution which is non-denaturing to the bovine somatotropin sample. The potency of the bovine somatotropin sample is determined based upon the level of biologically active bovine somatotropin protein so measured. In other embodiments, somatotropin is provided dissolved in a first buffer solution, and then chromatographed in a mobile phase comprised of a second buffer solution having a pH lower than the first buffer solution, to achieve an effective separation of biologically active protein from biologically-inactive large non-covalent soluble aggregates. The methods provide expedient, precise and accurate measures of the potency of somatotropin samples.

35 Claims, 24 Drawing Sheets

|     |                    |         |
|-----|--------------------|---------|
| 1.  | Thyroglobumin      | 660,000 |
| 2.  | r-globumin         | 166,000 |
| 3.  | BSA                | 66,000  |
| 4.  | Ovalbumin          | 45,000  |
| 5.  | B-Lactoglobumin    | 35,000  |
| 6.  | Carbonic anhydrase | 29,000  |
| 7.  | a-Chymotrypsinogen | 23,000  |
| 8.  | a-Lactalbumin      | 14,200  |
| 9.  | Ribonuclease A     | 13,700  |
| 10. | Insulin chain A    | 2,531   |

NON-DENATURING POTENCY ASSAY FOR SOMATOTROPIN

REFERENCE TO RELATED APPLICATIONS

This is a continuation-in-part of U.S. patent application Ser. No. 08/357,073 filed Dec. 15, 1994, now abandoned, which is a continuation of U.S. patent application Ser. No. 08/009,034 filed Jan. 26, 1993, now abandoned.

BACKGROUND

The present invention generally relates to somatotropins. More particularly, the present invention relates to non-denaturing methods for separating biologically active somatotropin protein fractions from somatotropin samples in a manner suitable to provide potency assays.

The production of bovine somatotropin (bST) and other somatotropins in large scale has recently been fostered by recombinant DNA technology. For example, recombinant microorganisms such as recombinant *Escherichia coli* produce insoluble granules of bST in their cytoplasm. These granules, known as refractile bodies or inclusion bodies, contain aggregated denatured somatotropin. The refractile bodies are recovered and usually treated with a denaturant such as guanadine hydrochloride, sodium dodecyl sulfate or urea. The denaturant unfolds and solubilizes the improperly folded bST molecules. Afterward, the bST molecules are renatured to form the properly folded, biologically active bST monomeric protein.

Due to inefficiencies of these denaturing and renaturing steps, however, some aggregates of improperly folded, biologically inactive somatotropin aggregates are also formed. Thus, the bST or other similar somatotropin bulk material obtained contains both the biologically active monomer and the biologically inactive aggregates. It is therefore important to establish a method for determining the potency of bST and other somatotropins in quality control.

The potency of bST and other somatotropins has previously been estimated by a rat weight gain method. Essentially, the weight gain of rats to which somatotropin samples are administered is monitored, and from this data a value representing the potency of the somatotropin is obtained. However, this assay cannot be employed to accurately quantify the somatotropins in routine analysis. Somatotropin potency has also been determined by radio receptor assay (RRA). However, RRA is time consuming. Also, RRA is inaccurate, and thus several tests are usually performed and the results averaged to provide a potency value.

Reversed-phase high performance liquid chromatography (RPHPLC) has been employed to determine proteins. However, most RPHPLC methods which have been used are not appropriate candidates for measuring the potency of bST because they have employed acidic mediums and organic solvents in the mobile phase, which denature bST.

Size exclusion high performance liquid chromatography ("size exclusion HPLC") using a mobile phase containing sodium dodecyl sulfate or guanadine hydrochloride has previously been employed to determine bST. However, such methods are not bio-potency assays because their mobile phases are denaturing to bST.

What is therefore needed are expedient, precise and accurate non-denaturing assays for determining the bio-potency of somatotropins. The present invention addresses these needs.

SUMMARY OF THE INVENTION

One preferred embodiment of the present invention provides a method for determining the potency of a bovine somatotropin sample. The method includes a first step of providing a bovine somatotropin sample dissolved in a first aqueous buffer solution having a pH above 8.5 and less than 12 and which is non-denaturing to the bovine somatotropin sample, said aqueous buffer solution being effective for dissolving both biologically-active bovine somatotropin and biologically-inactive bovine somatotropin non-covalently bonded aggregates (hereinafter "non-covalent aggregates") having a molecular weight above about 500,000 daltons. In a second step, the level of biologically-active bovine somatotropin in the bovine somatotropin sample is measured by size exclusion HPLC in a mobile phase which is non-denaturing to the biologically active bovine somatotropin and the biologically inactive somatotropin non-covalent aggregates, and under conditions which are effective to achieve separation of the biologically active bovine somatotropin from the biologically-inactive soluble aggregates. The method includes a further step of determining the potency of the bovine somatotropin sample based upon the measured level of biologically active bovine somatotropin.

One preferred mode of practicing the above-mentioned embodiment of the invention includes measuring the level of biologically active bovine somatotropin protein in the sample by size exclusion HPLC employing as a stationary phase a hydrophilic porous polymer gel having an average particle diameter of about 5 µm to about 15 µm and as a mobile phase a buffered aqueous solution having a pH of about 8 to about 12 and which is non-denaturing to the bovine somatotropin sample. The potency of the sample is determined based on the level of biologically active bovine somatotropin measured in the sample.

In another preferred mode, the above-mentioned embodiment of the invention is carried out including the steps of measuring the level of biologically active bovine somatotropin protein in the sample by size exclusion HPLC employing as a stationary phase a hydrophilic porous gel, for instance suitably including a silica or synthetic polymer gel, having an average particle diameter of about 5 µm to about 15 µm and as a mobile phase a buffered aqueous solution having a substantially neutral pH, for example a pH of about 7 to about 8, and which is non-denaturing to the bovine somatotropin sample. The potency of the sample is again determined based upon the level of biologically active bovine somatotropin protein measured in the sample. This aspect of the invention can also be used in potency determinations of other somatotropins, for instance mammalian somatotropins such as porcine and human somatotropins, which are thus also contemplated as being within this mode of carrying out the invention.

A further preferred embodiment of the invention provides a method for chromatographically treating somatotropin. This method includes a step of measuring the level of somatotropin monomer in a non-denatured somatotropin sample dissolved in a first aqueous buffer solution having a pH above 8.5 and less than 12, wherein the measuring includes subjecting the somatotropin sample to size exclusion HPLC employing as a stationary phase a hydrophilic porous gel having an average particle diameter of about 5 µm to about 15 µm and as a mobile phase a second aqueous buffer solution having a pH in the range of 7 to 8 and which is non-denaturing to the somatotropin sample.

A still further preferred embodiment of the invention provides a method for chromatographically treating bulk recombinant somatotropin. The method includes preparing a sample by reconstituting the somatotropin in a first aqueous borate buffer solution having a pH above 8.5 and less than 11, the first aqueous borate buffer solution being non-denaturing to the somatotropin and having a borate ion concentration of less than about 0.05M so as to be effective for dissolving any somatotropin occurring in the form of non-covalent somatotropin soluble aggregates with molecular weights above about 500,000 daltons. The level of somatotropin monomer in the sample is measured by size exclusion HPLC employing as a stationary phase a hydrophilic porous gel having an average particle diameter of about 5 µm to about 15 µm and as a mobile phase a second aqueous borate buffer solution having a pH in the range of 7 to 8, the second borate buffer solution also being non-denaturing to the somatotropin sample and having a borate ion concentration of less than about 0.05 M.

The invention provides methods that achieve advantageous separations of biologically active somatotropin protein from biologically inactive somatotropin forms. The methods are well adapted to serve in expedient, precise and accurate assays for determining of the potency of somatotropin samples. Additionally, for the first time, the separation and extensive characterization of somatotropin non-covalent soluble aggregates have been achieved using the inventive methods. Additional objects, features and advantages of the invention will be apparent from the description herein.

DESCRIPTION OF THE PREFERRED EMBODIMENT

Figure 1A:
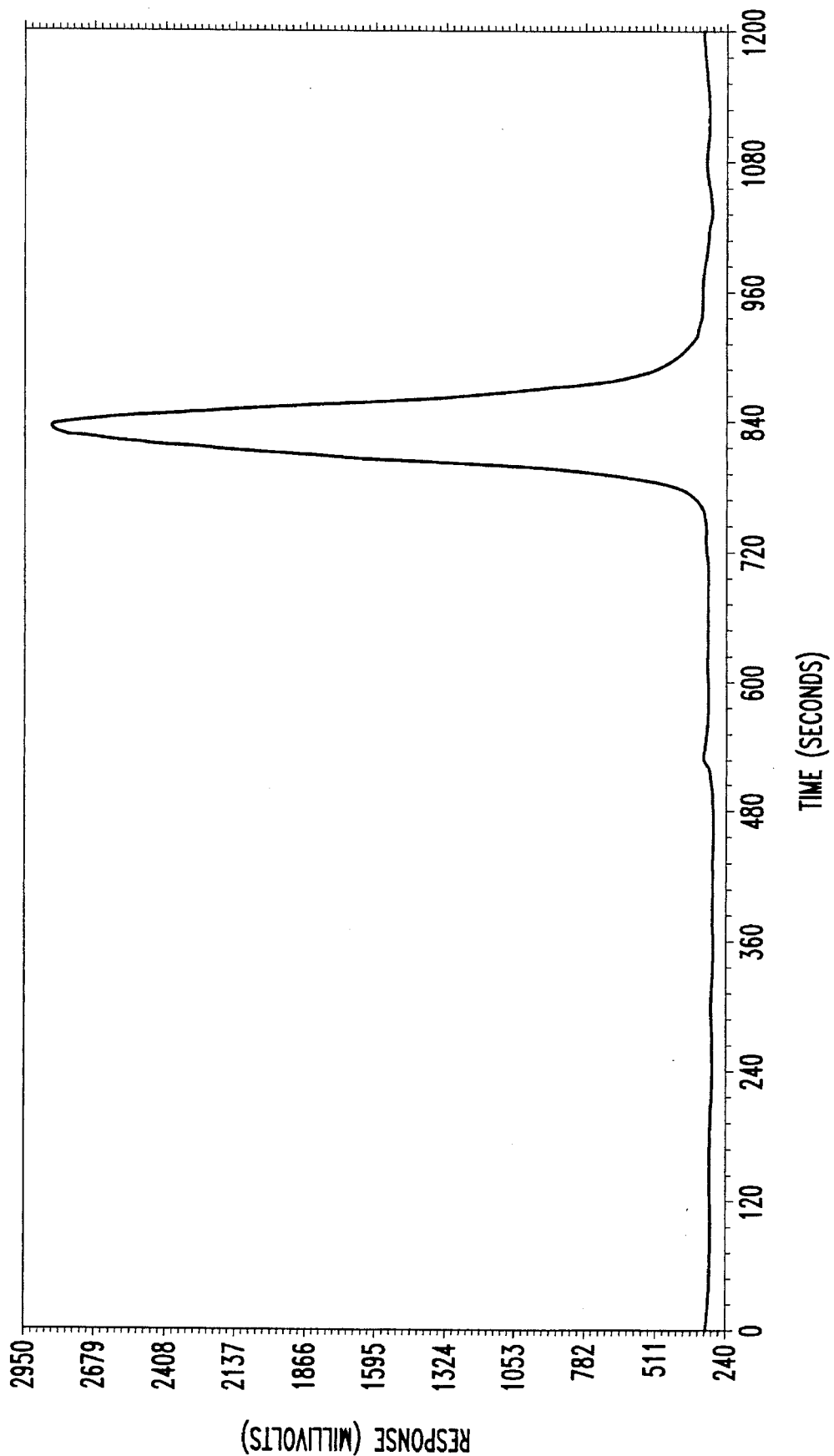
FIG. 1A is a size exclusion HPLC chromatogram of a biologically active bST reference standard using a bicarbonate mobile phase having a pH of 9 as further described in the Example 1, infra.

For the purposes of promoting an understanding of the principles of the invention, reference will now be made to a preferred embodiment thereof and specific language will be used to describe the same. It will nevertheless be understood that no limitation of the scope of the invention is thereby intended, such alterations, further modifications and applications of the principles of the invention as illustrated herein being contemplated as would normally occur to one skilled in the art to which the invention relates.

As indicated above, a preferred embodiment of the present invention relates to a method for separating a biologically active somatotropin fraction from somatotropin. As used herein, "somatotropin" denotes a substance, of natural or synthetic origin, which exhibits the properties of a natural somatotropin. The somatotropin can be extracted from appropriate glandular tissues of animals, e.g. pituitary glands; or, it is now well established practice to synthesize somatotropin and other such substances by the use of genetically-modified microorganisms such as bacteria. It is oftentimes convenient or even preferred that such processes yield a modified somatotropin, that is, a substance that differs as to its structure from the naturally occurring growth hormone, but which retains the biological activity of the naturally occurring growth hormone. For example, a modified somatotropin may contain one or more additional amino acids, at one or both ends of the polypeptide chain. Additional modifications will be understood by those skilled in the art. Therefore, the term somatotropin is used throughout this document to refer to both naturally occurring somatotropin as well as synthetically produced somatotropin which shares the biological properties of a naturally occurring somatotropin, and which may be identical or which may vary as to structure.

The present invention is preferred for use with mammalian somatotropins such as bovine somatotropin, porcine somatotropin (pST), or human somatotropin (hST). bST produced by recombinant DNA technology ("recombinant bST"), is an especially preferred material with which the present invention is used. Typically, the recombinant bST is obtained by isolating and denaturing and solubilizing inclusion bodies which contain the recombinant bST. The bST is then renatured to form the biologically active bST protein. During the denaturing/renaturing steps, biologically inactive bST non-covalent aggregates are formed along with the desired biologically active bST protein. Colloids and some very high molecular weight impurities can be removed from the solubilized inclusion bodies by ultrafiltration. However, substantial quantities of biologically inactive bST non-covalent aggregates usually pass through the ultrafilter along with the biologically active bST protein. As a result, the finally-obtained bulk recombinant bST contains biologically active bST protein as well as biologically inactive bST soluble aggregates. Recombinant hST and pST similarly form large, biologically inactive hST or pST aggregates. The method of the present invention can be used to treat these bulk recombinant somatotropins to separate the biologically active somatotropin protein from the biologically inactive somatotropin non-covalent soluble aggregates. Further, this separation is achieved in a manner which can be used to provide an expedient, precise and accurate assay for the potency of the bulk somatotropin material.

Two examples of recombinant bSTs are the compounds known as somidobove and sometribove. The present invention is especially preferred for application to these two recombinant bSTs.

The preferred methods of the invention employ size exclusion HPLC using as the stationary phase a hydrophilic porous gel. Preferred porous gels for use in the invention have an average particle diameter of about 5 μm to about 15 μm, and more preferably about 10 μm to about 15 μm. Typically, the average pore diameter of the gel will be about 100 to about 200 angstroms, and for the present invention a gel having an average pore diameter of about 150 angstroms is preferred. In another aspect, the porous gel used in the invention preferably has an exclusion limit average molecular weight greater than the molecular weight of the bST non-covalent soluble aggregate, e.g. about $10^6$ or greater, and more preferably about $10^7$ or greater. The porous gel can be formed of any suitable material for the separation, for example including synthetic polymers such as crosslinked polyethers, silica gels, and the like.

In one aspect of the invention, the mobile phase is an aqueous buffer solution having a pH of about 8 to about 12 and which does not denature the bST sample. Generally, the buffer may be included in the mobile phase at any effective concentration so long as the ionic strength of the mobile phase remains sufficiently low to avoid salting out of protein from the bST sample. Aqueous bicarbonate ($HCO_3-$) and aqueous borate buffer solutions, for example provided as an aqueous solution of ammonium bicarbonate or of sodium borate, provide preferred mobile phases. The bicarbonate buffer is desirably at a concentration of less than about 0.7M, and more preferably in the range of about 0.1 to about 0.4M. The borate buffer is desirably at a concentration of less than about 0.05M, for example in the range of about 0.001 to 0.05M.

The pH of the mobile phase will generally be in the range of about 7 to about 12. In one aspect of the invention, the mobile phase pH is more preferably about 9 to about 11, and most preferably about 9 to about 10. At these pH's, the bST soluble aggregates will remain in solution in the mobile phase for extended periods of time. When such pH's are used, it is preferred to also use a synthetic polymer-based HPLC gel as the stationary phase, which is stable against degradation at higher pH's. For example, a crosslinked polyether gel, such as that utilized in Example 1 below, is suitable.

In another aspect of the invention, the pH of the mobile phase is in the range of about 7 to about 8, more preferably about 7 to about 7.5. At these pH's, the bST soluble aggregates in reconstituted samples generally will not be solubilized; however, it has surprisingly been discovered that when delivered into solutions having pH's of about 7 to about 8 from solutions of higher pH's, for example above 8.5, the bST soluble aggregates will remain in the pH 7–8 buffer solutions for a period of time sufficient to enable a separation from biologically active bST over an HPLC column. Thus, a bST sample can be prepared in a buffer solution in which the bST soluble aggregates are solvated, for example a buffer solution having a pH above about 8.5. This sample is then processed on an HPLC column equilibrated with a mobile phase having a lower pH than that used to prepare the sample, for instance a pH of about 7 to about 8. Resulting chromatograms of the inventive processes demonstrate effective separation not only of the bST monomer and soluble aggregates, but also separation of the bST monomer and dimer from one another. Preferred HPLC columns for use at these relatively neutral pH's (about 7 to 8) will have stationary phases comprised of silica.

In this regard, the stationary phase is packed in a conventional HPLC column, which is a component of a conventional size exclusion HPLC set-up. For example, size exclusion HPLC set-ups typically include pumps, reservoirs for the aqueous buffer solution, an ultra violet (UV) absorption detector and a fraction collection means.

The bST sample to be treated by the method of the invention is preferably provided dissolved in an aqueous buffer solution, which can be identical to or different from that used as the mobile phase. The sample can be prepared by reconstituting bulk somatotropin the the buffer solution. In addition, it has been found that the aqueous buffer solution can be used to extract somatotropin from formulated somatotropin products containing hydrophobic carriers such as oils and/or waxes, so as to provide a sample suitable for the HPLC assays and methods of the invention. Borate buffer solutions have demonstrated superior extraction characteristics in this regard and are preferred for use in this aspect of the invention.

Where the mobile phase to be used is one in which the bST soluble aggregate is essentially indefinately soluble (e.g. generally having a pH above about 8.5), it is preferred that the buffer solution used as the mobile phase and to reconstitute the sample be the same. Where the bST soluble aggregate is insoluble in the mobile phase used, the buffer solution for the mobile phase and to reconstitute the sample will have differing pH's. That is, the pH of the reconstituting buffer will be higher than that of the mobile phase, to achieve dissolution of the bST soluble aggregates in the prepared sample.

The concentration of bST in the sample is desirably about 0.05 to about 2 milligrams per milliliter (mg/mL). More preferably, the bST concentration in the sample is about 0.1 mg/mL to about 1 mg/mL.

The pressure on the size exclusion HPLC column provides a suitable flow rate for separations performed in accordance with the invention. The pressure necessary to achieve advantageous flow rates will of course be dependent upon the particle size of the stationary phase. In preferred methods of the invention, the pressure and the resulting flow rate used in the size exclusion HPLC will completely elute the biologically active bST protein fraction within about 30 minutes so as to provide an expedient assay. In this regard, typical column pressures are about 500 to about 1500 psi, and more typically about 800 to about 1000 psi.

Figure 5:
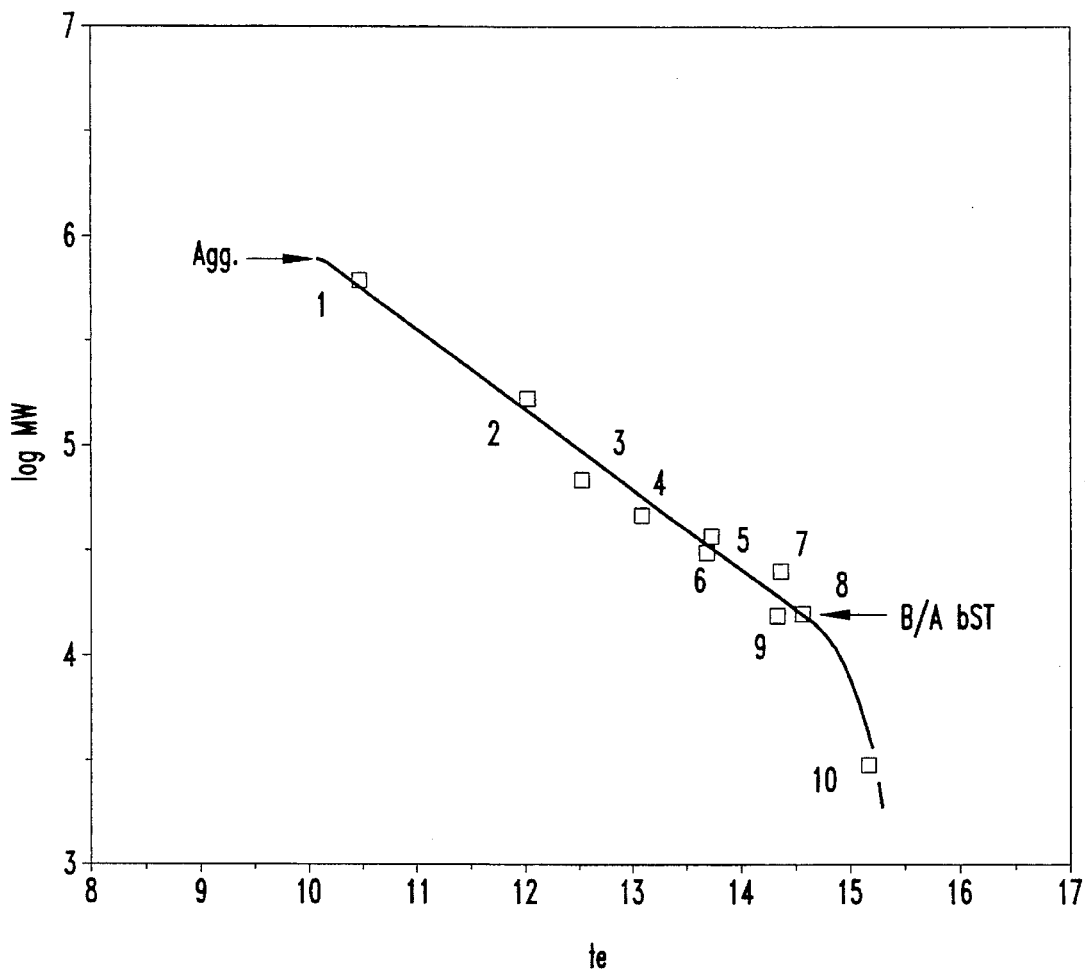
FIG. 5 is a size exclusion HPLC calibration curve of log MW vs. elution time for standard proteins and the biologically active bST protein ("B/A bST") and bST soluble aggregate ("Agg.") under conditions described in the Example 1, infra.

In another aspect of the applicant's work, using the above-described non-denaturing size exclusion HPLC method, a bST soluble aggregate of high molecular weight has been isolated and extensively characterized. In FIGS. 1B and 1C, the peak excursions beginning at about 9 minutes contain these high molecular weight bST soluble aggregates. The molecular weight of these bST soluble aggregates is greater than 660,000 as determined by size exclusion HPLC (FIG. 5). The bST soluble aggregates are biologically inactive as determined by radio receptor assay.

Figure 6:
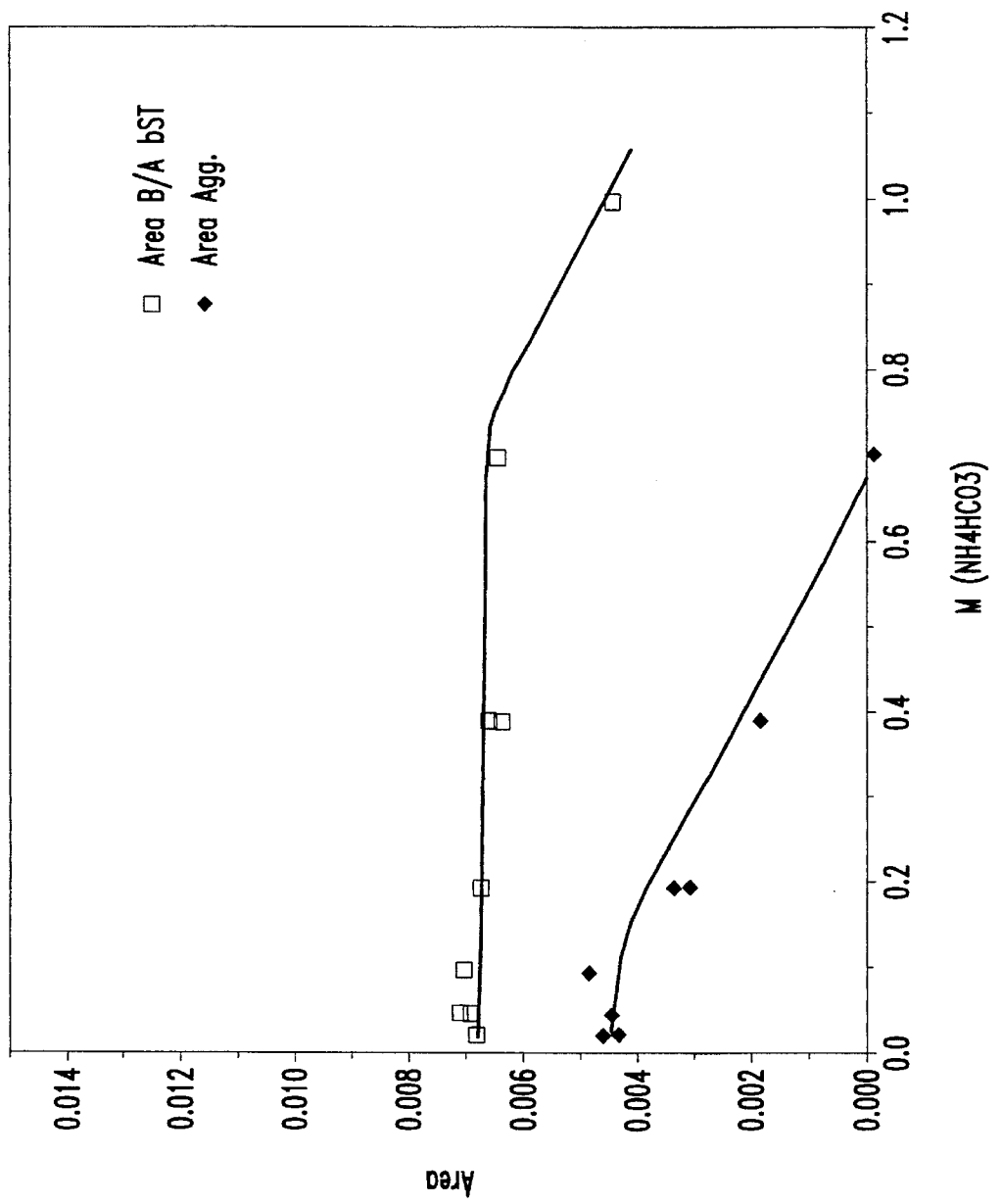
FIG. 6 is a graph showing the effect of ammonium bicarbonate concentration on the size exclusion HPLC peak area response for the biologically active bST protein fraction ("B/A bST") and for the fraction including the bST soluble aggregate ("Agg.") under conditions described in the Example 1, infra.
Figure 7:
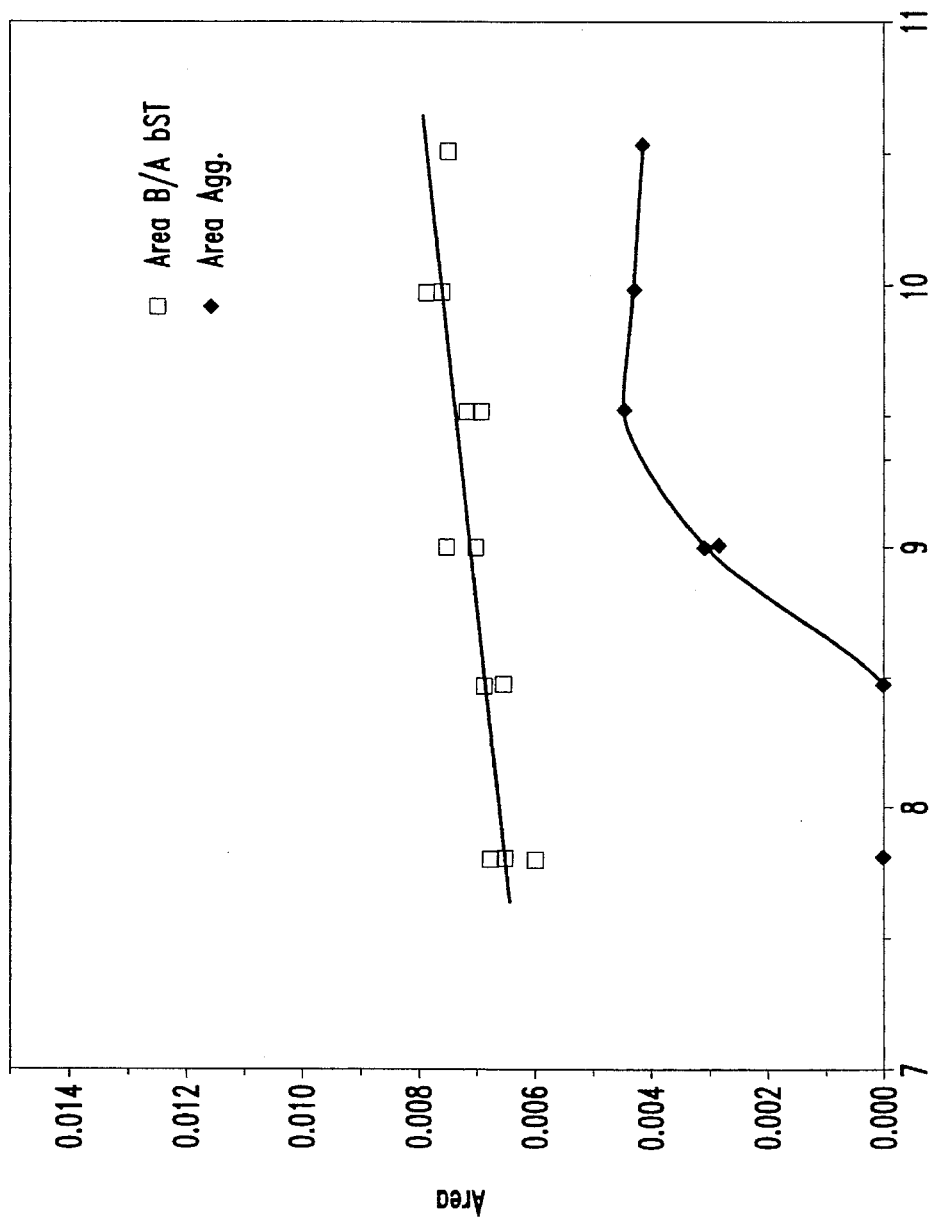
FIG. 7 is a graph showing the effect of bicarbonate mobile phase pH on the size exclusion HPLC peak area for the biologically active bST protein fraction ("B/A bST") and for the fraction including the bST soluble aggregate ("Agg.) under the conditions described in the Example 1, infra.
Figure 8:
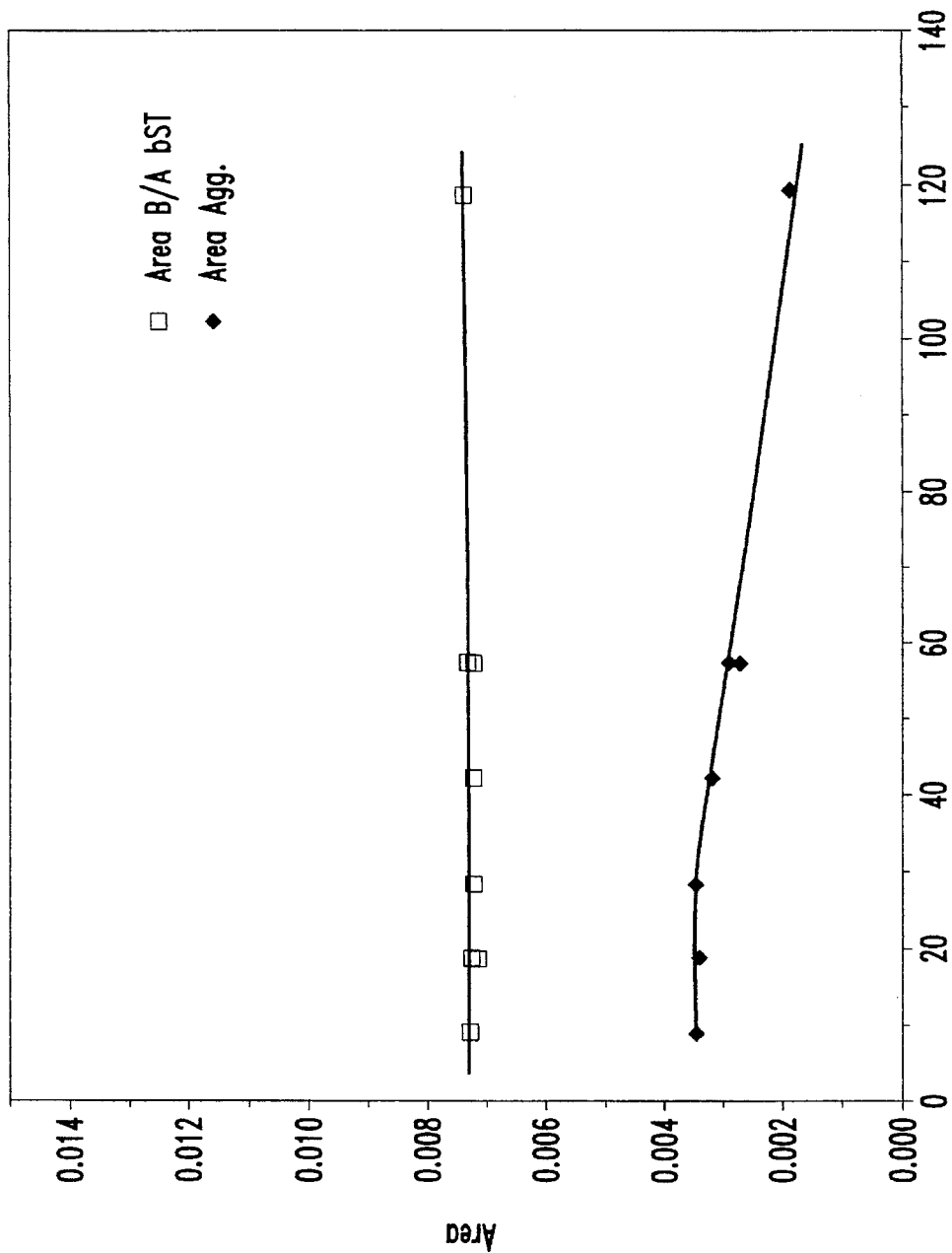
FIG. 8 is a graph showing the effect of centrifuging on the size exclusion HPLC peak area of the biologically active bST protein fraction ("B/A bST") and of the fraction including the bST soluble aggregate ("Agg.") under the conditions described in the Example 1, infra.

The behavior of this bST soluble aggregate in solution has also been characterized. The bST soluble aggregate is substantially soluble in non-denaturing aqueous buffer solutions having pH's greater than about 8.5 and less than about 12 (FIGS. 1D, 1E and 7). At pH's outside this range, the soluble aggregate precipitates from non-denaturing aqueous buffer solutions. High salt concentration will also cause the bST soluble aggregate to precipitate (FIG. 6). For instance, salting out of the bST soluble aggregate is observed at bicarbonate concentrations above about 0.7M. Moreover, under centrifuging at 16,000 times the force of gravity ("16,000 g"), the bST soluble aggregate remains in 0.2M bicarbonate buffer solution (pH 9) for 30 minutes or more (FIG. 8). Denaturing agents such as sodium dodecyl sulfate and urea will denature the bST soluble aggregate to monomeric bST. These and other characteristics of the bST soluble aggregate are discussed further in the Examples, infra.

In order to promote a further understanding of the invention, the following specific Examples are provided. It will be understood that these Examples are illustrative and not limiting in nature.

EXAMPLE 1

Chemicals and Reagents

All reagents were of analytical-reagent grade and were used without further purification. Water was obtained from a Millipore Milli-Q water purification system. The bST reference standard and recombinant bST bulk materials (somidobove) were from Eli Lilly and Company.

Conditions of Size Exclusion HPLC Chromatography

A rigid porous polymeric gel having a plurality of hydrophilic groups (the gel was a crosslinked hydroxylated polyether) and having an average particle size of about 10 μm (tradename, Beckman Spherogel TSK 3000 PW column (600×7.5 mm, I.D.)) was employed in these Examples. The mobile phase for separations reported herein was 0.2M ammonium bicarbonate adjusted to pH 9 with NaOH, unless otherwise indicated. All separations were achieved at room temperature and at a flow rate of 0.5 mL/min. (generating a corresponding pressure in the range of about 800 to 1000 psi) unless otherwise indicated. The sample injection volume was 20 μL. Most separations were performed using the Waters 625 LC system with a 911+ photodiode array detector and a WISP 721 autosampler. However, the precision and linearity studies were carried out on a Beckman System-Gold HPLC system consisting of a Model 126 solvent delivery system, a Model 166 variable wavelength detector, and a Model 507 autosampler.

Sample Preparation

Samples and standards were prepared in the mobile phase. All bST samples were prepared at a concentration of ~1 mg/mL bST unless otherwise indicated. To minimize incomplete dissolution, an aliquot of mobile phase was added to the bST and the sample solution was allowed to stand at room temperature for 30 minutes. Thereafter, the sample solution was gently shaken for 5 to 10 minutes. Sample solutions were then filtered through an Acrodisc 0.45 mm filter prior to injection.

Results of Size Exclusion HPLC of bST Samples

Figure 1B:
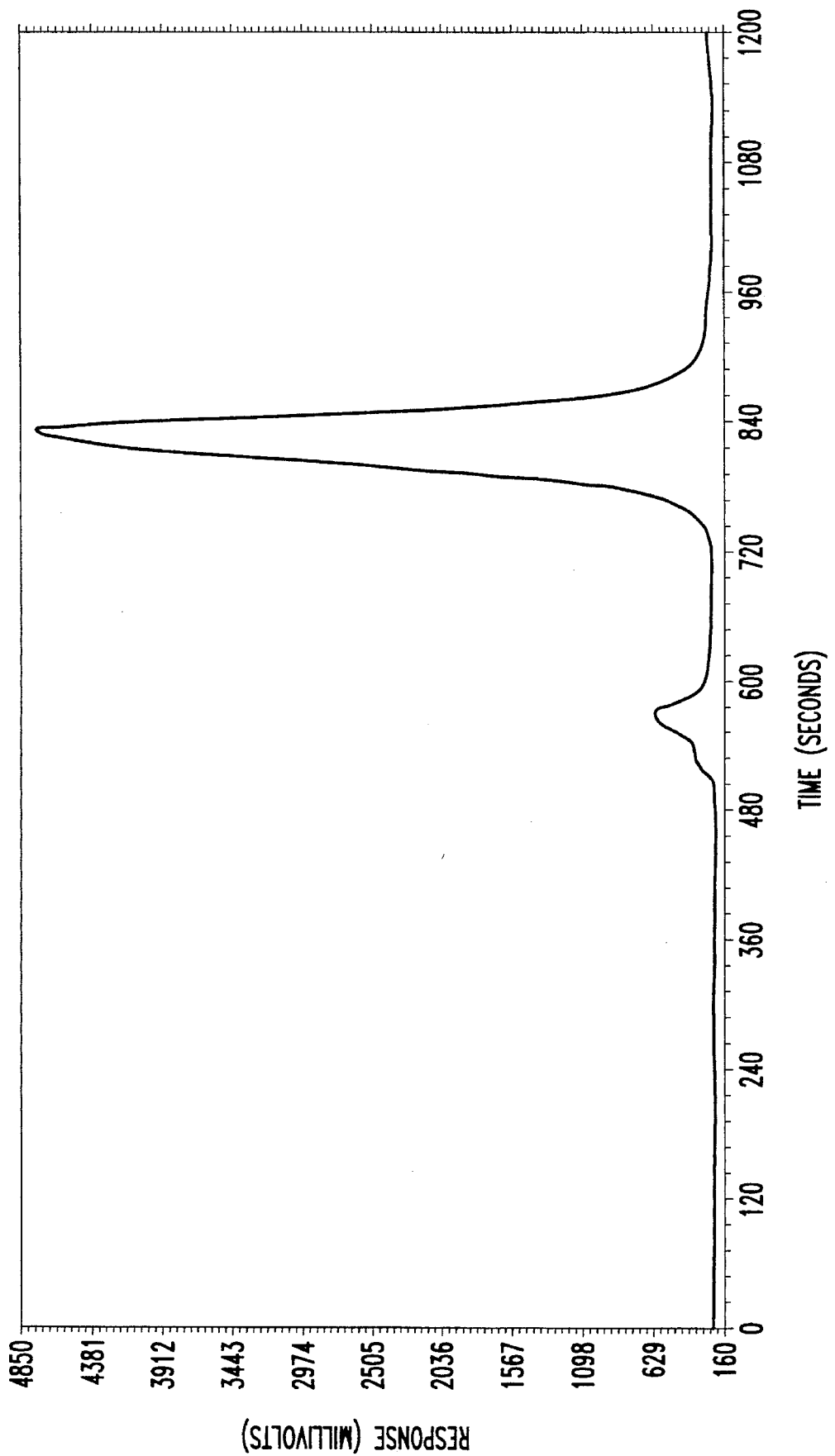
FIG. 1B through 1E are size exclusion HPLC chromatograms of bulk recombinant bST materials using a bicarbonate mobile phase having a pH of 9 as further described in the Example 1, infra, and demonstrating the presence of bST soluble aggregates in the bulk materials.
Figure 1C:
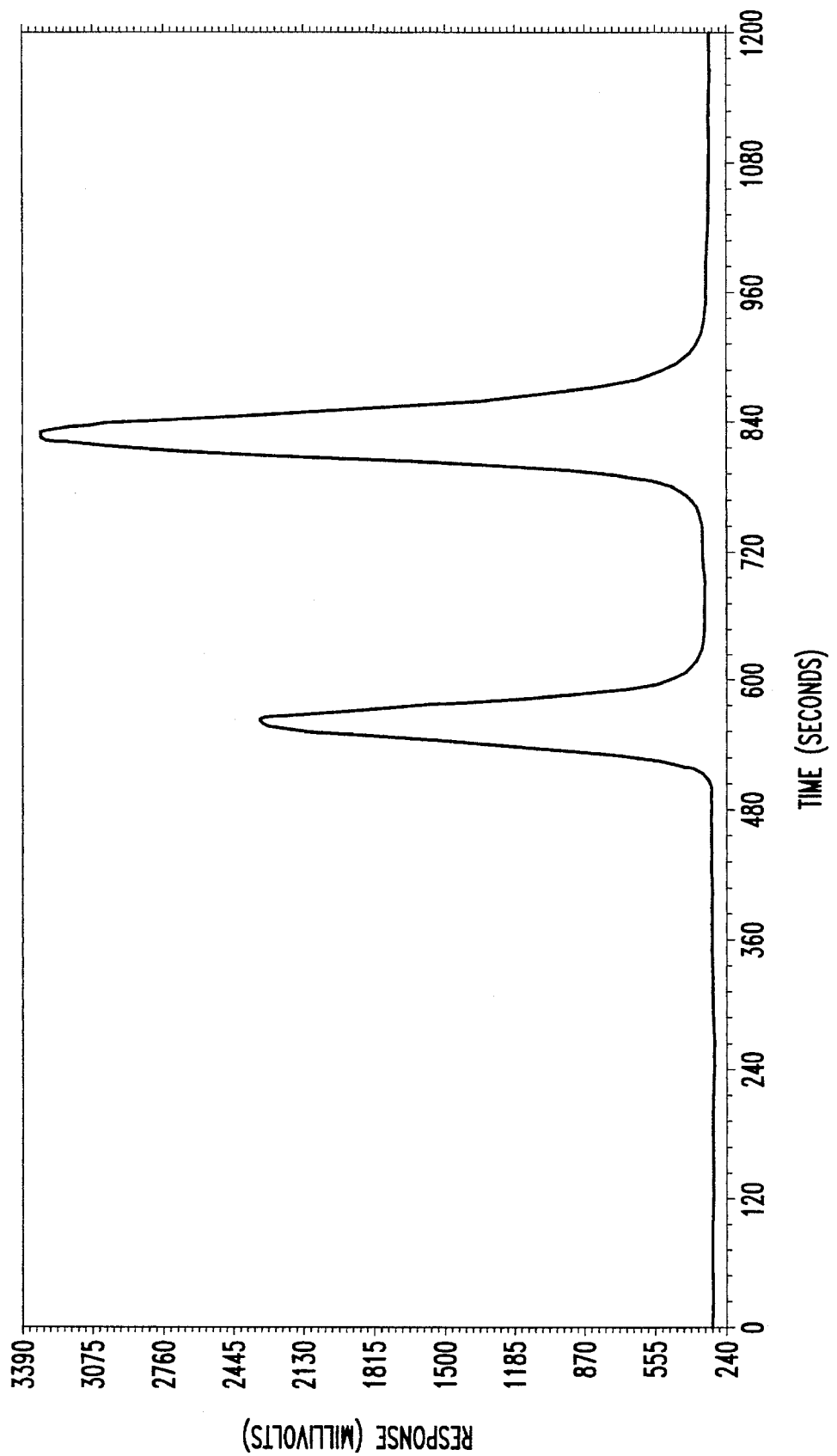
Figure 1D:
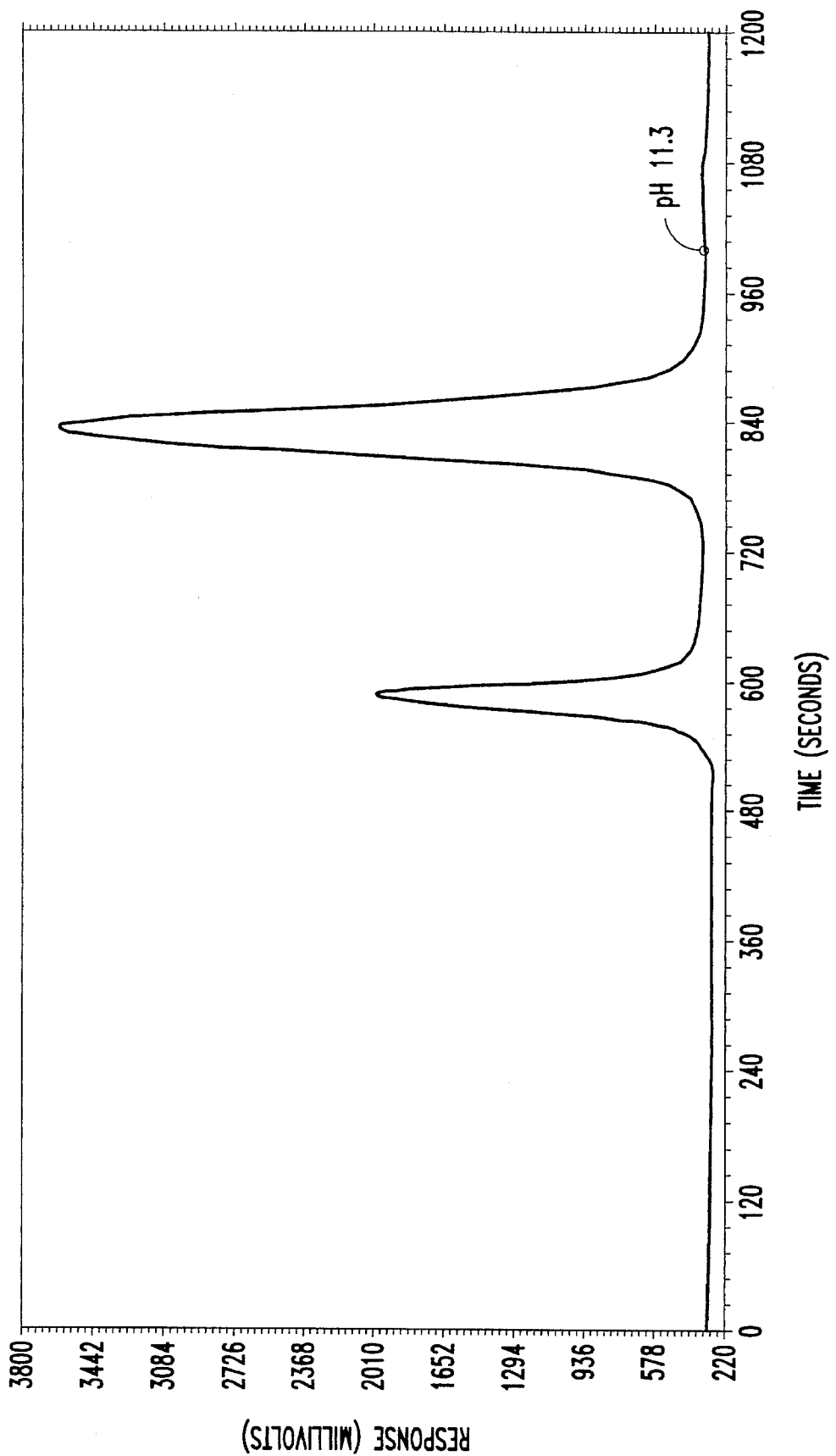
Figure 1E:
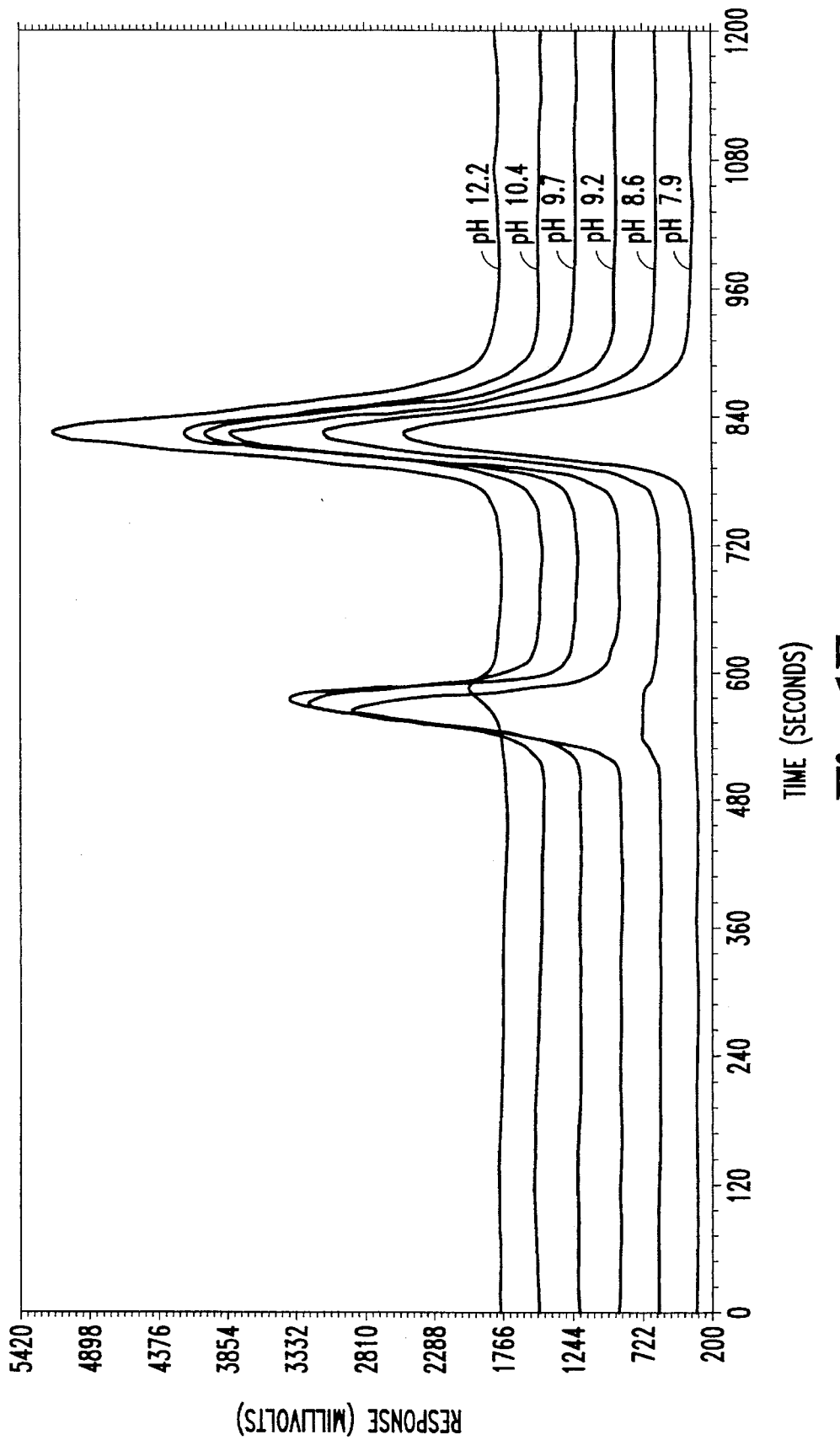

FIG. 1A shows a size exclusion HPLC chromatogram of a biologically active recombinant bST protein reference standard in which only a single main peak containing biologically active bST protein was found. The chromatogram of FIG. 1A was obtained using the methodology described above, except the flow rate was 1 mL/min. FIGS. 1B and 1C show size exclusion HPLC chromatograms of different lots of recombinant bST bulk material. Two strong peaks with excellent baseline resolution between them were observed. The chromatographic first eluting peak (N9 min) contains the high molecular weight bST soluble aggregates, and the second eluting peak (N13 min) is biologically active bST protein.

FIGS. 1D and 1E show size exclusion chromatograms of samples from the same bulk recombinant bST used in preparing the chromatogram of FIG. 1C. The lone chromatogram shown in FIG. 1D was taken with a mobile phase having a pH of 11.3. Two strong peaks were again observed as in FIG. 1B. The superimposed chromatograms of FIG. 1E were developed using mobile phases having pH's ranging from 7.9 to 12.2. Diminished peak area response at the lower and higher pH's which were studied evidenced the diminished solubility of the bST soluble aggregate. More advantageous methods of the invention are performed using mobile phase pH's where higher solubility of the bST soluble aggregate exists, e.g. in these runs at pH's between about 9 and about 12.

Additional size exclusion HPLC chromatograms of the lots shown in FIGS. 1B and 1C were taken under the same conditions except using a different non-denaturing mobile phase (0.05M borate buffer solution). The chromatograms obtained were similar to those shown in FIGS. 1B and 1C, having two strong peaks and good baseline resolution between them. Thus other non-denaturing aqueous buffer solutions may be readily employed in size exclusion HPLC separations according to the invention.

Varying Size Exclusion HPLC conditions

Figure 2A:
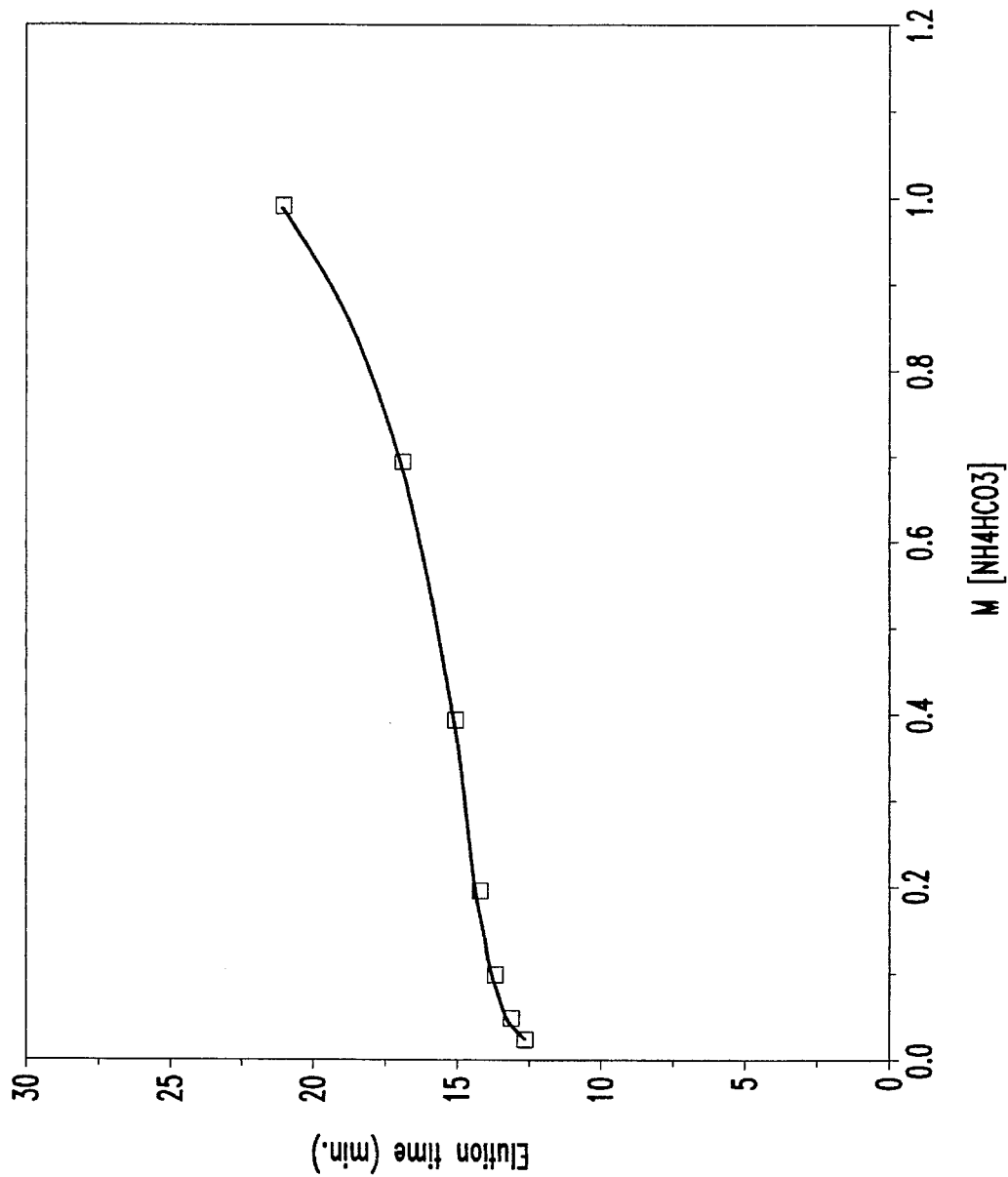
FIG. 2A is a graph showing the effect of bicarbonate buffer concentration on the size exclusion HPLC retention time of the biologically active bST protein fraction using the methodology described in the Example 1, infra.
Figure 2B:
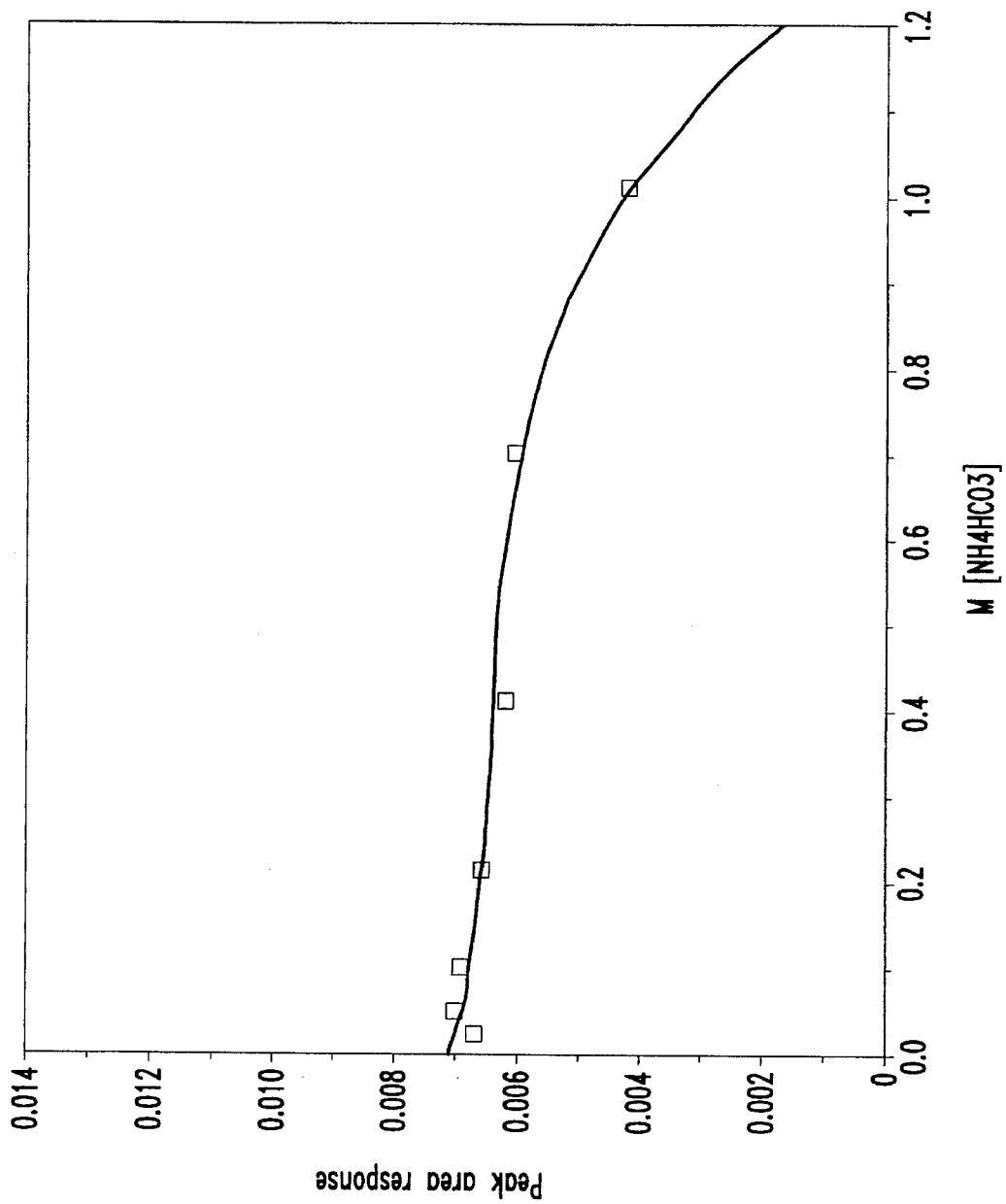
FIG. 2B is a graph showing the effect of bicarbonate buffer concentration on the size exclusion HPLC peak area response of the biologically active bST protein fraction under conditions described in the Example 1, infra.

The effect of varying ammonium bicarbonate concentration on elution time of the biologically active bST protein fraction in size exclusion HPLC was investigated. A series of experiments demonstrated that biologically active bST protein gave a typical size exclusion HPLC curve (FIG. 2A) upon varying the ammonium bicarbonate solution. A slight change in elution time was observed as the ammonium bicarbonate concentration ranged from about 0.1M to about 0.4M. Elution time increased more rapidly when the concentration of ammonium bicarbonate ranged above about 0.4M. Further, the peak area of bST significantly decreased when increasing salt (ammonium bicarbonate) concentration to higher than about 0.7M (FIG. 2B). Preferred size exclusion HPLC methods of the invention are thus performed using a bicarbonate salt concentration in the mobile phase of less than about 0.7M.

Figure 3A:
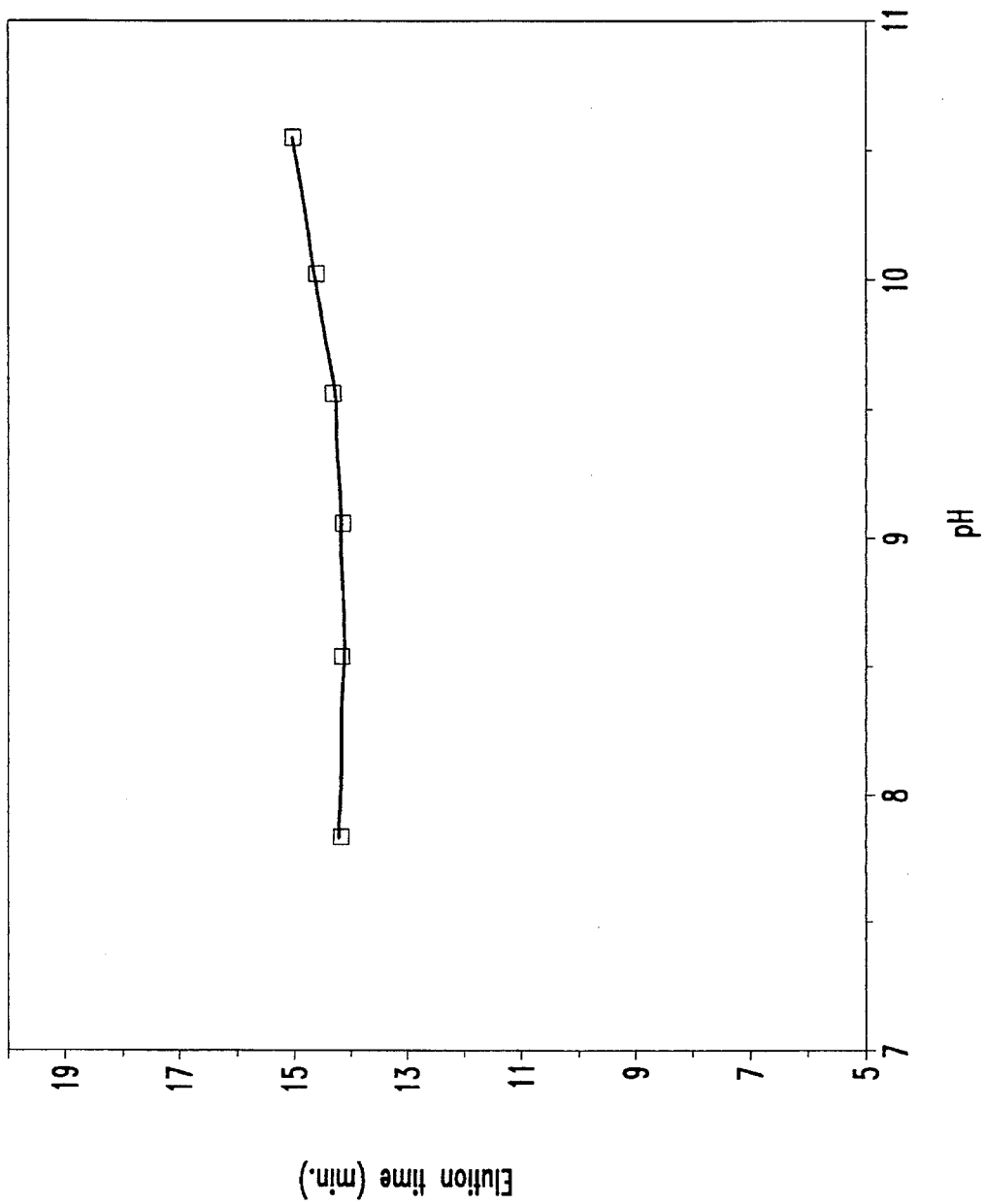
FIG. 3A is a graph showing the effect of mobile phase pH variation on the size exclusion HPLC elution time of the biologically active bST protein fraction using the methodology described in the Example 1, infra, FIG. 3B a graph showing is the effect of mobile phase pH variation on the size exclusion HPLC peak area response of the biologically active bST protein fraction using the methodology described in the Example 1, infra.
Figure 3B:
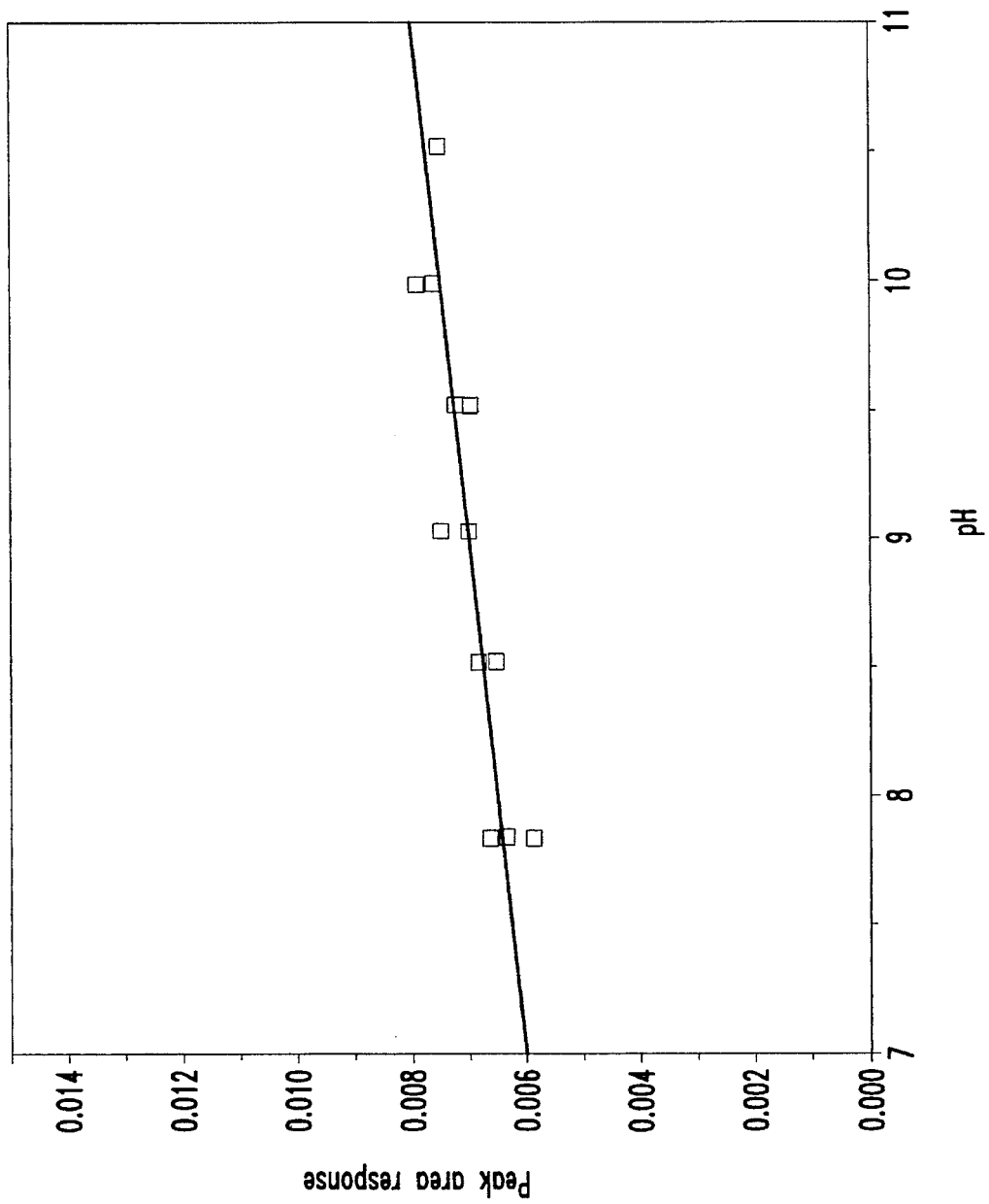

The effect of varying pH of the mobile phase on size exclusion HPLC elution time and peak area response of the biologically active bST protein fraction was also investigated. Increasing the pH of the 0.2M ammonium bicarbonate mobile phase in the range of about 7.5 to about 10.5 did not affect the elution time of bST; however, peak area response was slightly increased over the same pH range (FIGS. 3A, 3B).

The most advantageous size exclusion HPLC flow rate in this study was found to be about 0.5 mL/min. A flow rate of 0.3 mL/min. is usable and results in equivalent efficiency, but nearly doubles the run time. The biologically active bST protein peak overlapped with the void peak at 1 mL/min. flow rate.

Non-denaturation of bST Sample

In order to confirm that the inventive method is non-denaturing to the bST, the biologically active bST protein fraction in the reference standard (see FIG. 1A) was collected and its biological activity measured by RRA. The results indicated that the collected biologically active bST protein component in mobile phase retains equal biological activity to the parent solution before treatment by the size exclusion HPLC.

Figure 4:
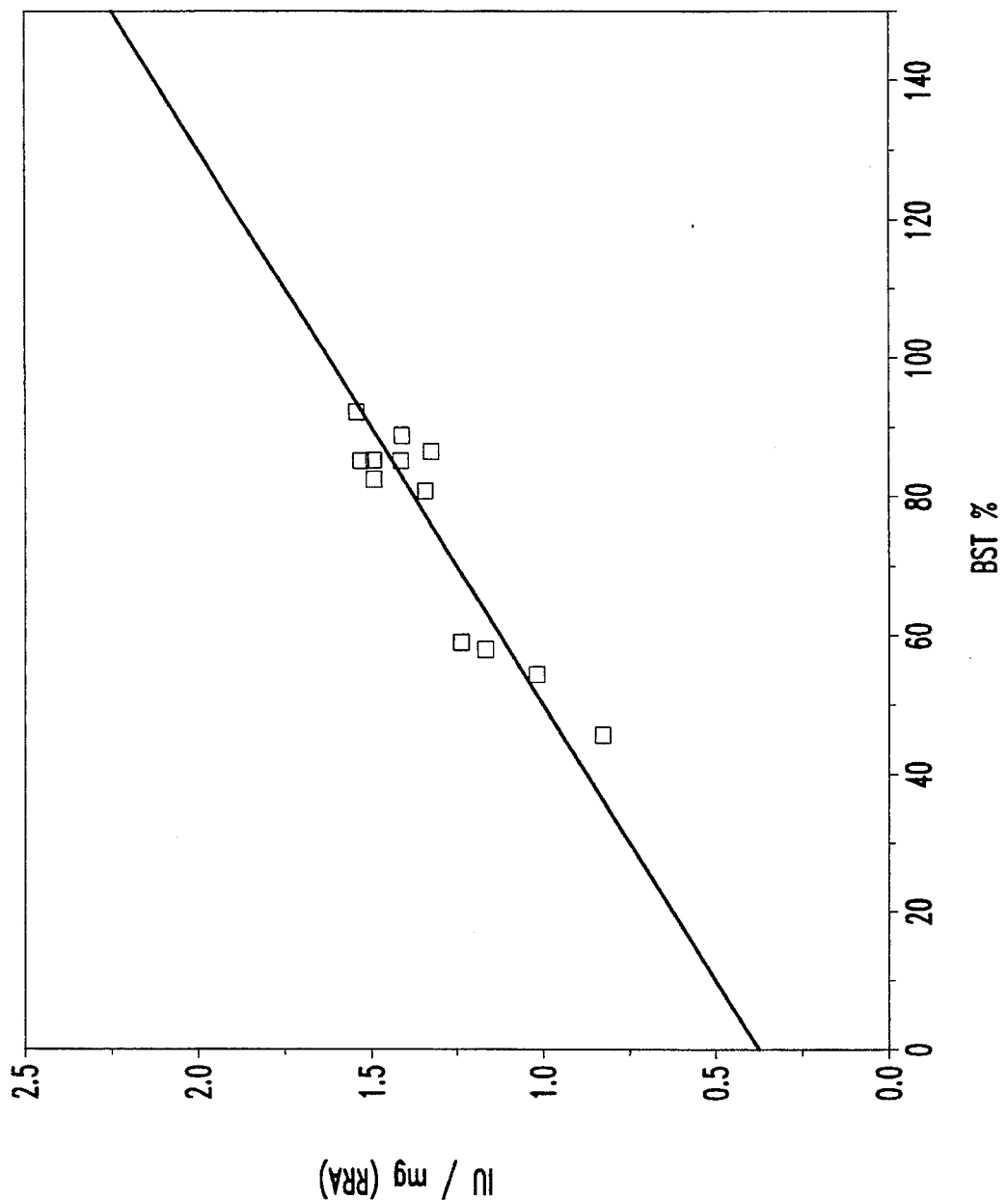
FIG. 4 is a graph showing the correlation between radioreceptor assay potency data (IU/mg) and the size exclusion HPLC-measured level of biologically active bST protein for several different lots of bulk recombinant bST under the conditions described in the Example 1, infra.

In testing of several different lots of recombinant bulk bST, a strong correlation was demonstrated between the level of biologically active bST protein measured by the inventive size exclusion HPLC method and the potency data (I.U./mg) measured by RRA. A linear regression plot of the data from the size exclusion HPLC method and RRA is shown in FIG. 4. The correlation coefficient for the data was 0.845. These results clearly demonstrate that the inventive size exclusion HPLC method can be used in a determination of the potency value of bST bulk materials. That is, the inventive size exclusion HPLC method can be used to measure the level (e.g. in peak area percent) of biologically active bST protein in a bST sample of unknown potency. The level of biologically active bST protein measured in the sample can then be plotted on a calibrated curve similar to that in FIG. 4, including data from RRA and size exclusion HPLC assays on bST controls. RRA data correlates well to bio-potency data obtained by still other methods, for example the well known rat weight gain method. Thus, a similar correlation of the size exclusion HPLC results can be made to data obtained by other known bST bio-potency assays.

Linearity And Precision of Method

The linearity of the inventive size exclusion HPLC method was measured by preparing varying concentrations of biologically active bST protein reference standard in mobile phase. Standard solutions in the bST concentration range of 0.1 to 1 mg/mL treated by size exclusion HPLC in triplicate and a linear regression analysis of the data performed. The reproducibility of the linearity obtained using three different columns in three different days is shown in Table 1. The correlation coefficient ranged from 0.9998 to 1.000, and the average relative standard deviation (R.S.D.) was 1.36%.

TABLE 1

| Slope | 306600 | 301200 | 311400 |
|---|---|---|---|
| R.S.D. % | 0.60 | 1.51 | 0.77 |
| Y-Intercept | −3940 | −2050 | −3270 |
| Correlation coefficient | 1.0000 | 0.9998 | 0.9999 |

The precision of the inventive size exclusion HPLC method was evaluated over three days while using two different HPLC systems, three columns with different series numbers, and three different lots of bST bulk materials. The resulting data, shown in Table 2, demonstrate that the R.S.D. of biologically active bST protein measured is less than 2.8%, and the reproducibility of elution time is less than 0.18% R.S.D.

TABLE 2

| Lot | Day | n | Beckman System | | | | Waters System | | | |
|---|---|---|---|---|---|---|---|---|---|---|
| | | | % bST | % RSD | te | % RSD | % bST | % RSD | te | % RSD |
| 001 | 1 | 3 | 83.5 | 0.70 | 851 | 0.12 | 83.8 | 2.67 | 827 | 0.07 |
| | 2 | 3 | 81.7 | 1.27 | 831 | 0.09 | 83.7 | 0.91 | 846 | 0.07 |
| | 3 | 3 | 82.7 | 0.75 | 822 | 0.10 | — | — | — | — |
| 002 | 1 | 3 | 87.1 | 2.23 | 849 | 0.18 | 86.1 | 2.80 | 824 | 0.15 |
| | 2 | 3 | 86.1 | 2.72 | 830 | 0.06 | 86.7 | 2.56 | 850 | 0.09 |
| | 3 | 3 | 88.9 | 1.34 | 824 | 0.10 | — | — | — | — |
| 003 | 1 | 3 | 44.9 | 0.47 | 853 | 0.08 | 44.5 | 2.40 | 827 | 0.10 |
| | 2 | 3 | 46.3 | 1.14 | 837 | 0.13 | 46.9 | 1.32 | 854 | 0.17 |
| | 3 | 3 | 46.8 | 0.75 | 829 | 0.10 | — | — | — | — | n = Replicate Number
te = Retention Time (in seconds)
RSD = Relative Standard Deviation A bST recovery study was carried out by the addition of biologically active bST protein reference standard in two different concentrations to two different to bulk bST. The recoveries obtained in this experiment ranged from 101 to 104% (Table 3).

TABLE 3

| Sample | Reference Standard Added (mg) | Found (mg) | n | Recovery (%) | RSD (%) |
|---|---|---|---|---|---|
| 003A | 0.186 | 0.191 | 3 | 102.5% | 0.34 |
| 003A | 0.465 | 0.471 | 3 | 101.2% | 0.58 |
| 003B | 0.186 | 0.193 | 3 | 103.8% | 0.90 |
| 003B | 0.465 | 0.472 | 3 | 101.4% | 0.72 | n = Replicate Number
RSD = Relative Standard Deviation

The above results demonstrate that the inventive size exclusion HPLC method provides for the accurate and precise determination of bST potency in bulk bST materials.

bST Soluble Aggregate Characterization

As indicated above, a peak at about 13 min. represents the biologically active bST protein fraction and a peak at about 9 min. represents a bST soluble aggregate fraction (FIGS. 1B–1E). In further work, a UV spectrum taken by photodiode array detector in the size exclusion HPLC process demonstrated that the UV profiles of the biologically active bST protein fraction and bST soluble aggregate fraction were similar. A UV spectral change of the bST soluble aggregate was noted at 250–270 nm, and may be due to a change in the environment of the aromatic amino acids after aggregation.

The molecular weight of bST soluble aggregates was measured by a calibration curve using size exclusion HPLC. The results are shown in FIG. 6. The bST soluble aggregate eluted at the exclusion volume of the column and its molecular weight (MW) was higher than 660,000 (MW of thyroglobumin).

To further characterize the bST soluble aggregate, bulk bST was dissolved in 0.4M ammonium bicarbonate (pH 9) to make a 5 mg/mL solution. After centrifugation at 16,000 g, the supernatant was treated under the standard size exclusion HPLC conditions described above except the mobile phase was a 0.4M ammonium bicarbonate solution. Two components obtained in this separation, biologically active bST protein and bST soluble aggregates, were collected in separate fractions. Each collected fraction was re-chromatographed to confirm its elution time and purity. The results demonstrated that the bST aggregate remained in solution even after the centrifugation.

Experiments were performed to confirm that the bST soluble aggregate is non-covalently bonded. If the bST soluble aggregate were a non-covalent bonded protein, it would dissociate into monomer in the presence of denaturing agents such as detergents, high concentration urea and guanadine HCl in solution. To confirm this, a 1:1 mixture of the collected bST soluble aggregate fraction with 2% sodium dodecyl sulfate (SDS) was chromatographed in a system including a du Pont 250 column and a 0.4M bicarbonate mobile phase containing 1 SDS. As expected, the chromatographic profile and UV-spectrum of the dissociated proteins was identical to that of SDS-monomer obtained under the same experimental conditions. In similar experimentation it was demonstrated that the bST soluble aggregates can also be dissociated by 3M urea.

Additional behaviors of bST soluble aggregates in solution have been investigated. The solubility of the bST soluble aggregates was strongly affected by salt concentration in solution. Increasing bicarbonate concentration sharply decreases the solubility of soluble aggregate due to salting-out of the proteins as shown by size exclusion HPLC under the above-noted conditions except varying the concentration of ammonium bicarbonate in the prepared sample and mobile phase, as indicated in FIG. 6. Similarly, the effect of the pH of the bicarbonate buffer solutions on the solubility of the bST soluble aggregate was investigated. At pH less than 8.5 and pH greater than 12.5, bST soluble aggregate precipitates out of the 0.2M bicarbonate solution. Solubility of the bST soluble aggregate increased with increasing pH starting from pH 8.5, and reached a maximum at pH 9.5 (FIG. 7).

The stability of the soluble aggregates in bicarbonate solution was also studied. The isolated bST soluble aggregate solution is stable for two days at 4° C., and for more than 9 hours at room temperature (as determined by measuring size exclusion HPLC peak area over time). Additionally, when centrifuging at 16,000 g, the bST soluble aggregate remains in solution for at least 30 minutes (FIG. 8).

EXAMPLE 2

Chemicals and Reagents:

Unless otherwise indicated in the discussions which follow, the chemicals and reagents employed in this Example 2 were the same as those employed in Example 1.

Conditions of Size Exclusion HPLC Chromatography

High performance size exclusion chromatography was performed on an HPLC system consisting of a Waters 625 LC system with a 991+ photodiode array detector and WISP 712 autosampler (Waters Chromatography, Milford, Mass. U.S.A.). The column employed was a TSK G3000SW column (21.5 mm×300 mm, TosoHasso, Montgomeryville, Pa. U.S.A., operated at ambient temperature and with a 20 μL injection volume. A flow rate of 0.5 mL/min. was employed for most of the studies. The mobile phase was 20 mM sodium borate—1.44 mM EDTA buffer solution adjusted to pH 7.3 with hydrochloric acid, except where specified. Elutes were detected at 280 nm. A linear regression plot of the reference standard in mg/mL versus peak area was used to quantify rbST monomer in samples. Peak area normalization was employed for the estimation of dimer and aggregates. Chromatographic data were collected, stored and analyzed by a HP-1000 computer system (Hewlett-Packard, San Fernando, Calif. U.S.A.).

Sample Preparation

A 20 mM sodium borate—1.44 mM EDTA buffer solution adjusted pH to 9.5 with sodium hydroxide was used as a sample solvent to dissolve bulk drug substances and reference standard. Samples were prepared at a concentration range between 0.3–0.8 mg/mL for analyses. In order to minimize incomplete dissolution, an aliquot of the buffer solution was added to the bulk drug substance and allowed to stand at room temperature for 40 minutes. The solution was then gently shaken for 5 minutes until completely dissolved and then diluted to volume.

Isolation of dimer

A 10 mg/mL concentration of rbST bulk substance was prepared in the sample solution. An aliquot of 400 μL of this solution was injected into the semi-preparative HPLC system consisting of a TSK G3000SW semi-preparative column and the same mobile phase used for analytical purposes. The isolation was carried out at a 2.5 mL/min. flow rate. The dimer fractions were collected and dialyzed against 5 mM ethylenediamine for 24 hours. The dimer solution was then lyophilized.

Reversed phase high performance liquid chromatography (RPHPLC)/electro-spray mass spectrometry (ESP-MS)

A gradient elution with trifluoroacetic acid (TFA)/acetonitrile (ACN) solvent system was used in RPHPLC/ESP-MS for the molecular weight measurement of rbST monomer and dimer. Solvent A was 0.1 percent TFA in 35 percent ACN/water and solvent B was 0.1 percent TFA in 70 percent ACN/water. A 30-minute linear gradient from 0 to 100 percent solvent B at 1 mL/min. flow rate was used to separate samples on a Vydac 218TP104 column. The LC/MS experiment was conducted on a Sciex API LC-MS system (Perkin-Elmer/Sciex, Toronto, Canada). The split ratio was constant at 99.5 to 0.5 with 0.5 percent of the total post-column effluent introduced into the ESP-MS interface in ESP-MS system. The other 99.5 percent passed through the flow cell of a Waters 487 tunable absorbance detector and the signal was monitored simultaneously at 214 nm with the acquisition of MS data.

Deconvolution of charged states and assignment of total molecular mass was achieved with the aid of the "Hypermass" feature included with the MacSpec mass spectral data manipulation package (Sciex, Inc.). Marker ions detected in the assigned scan range were used to extrapolate mass/charge relationship to determine accurate mass for the components studied.

HPSEC column

Figure 9:
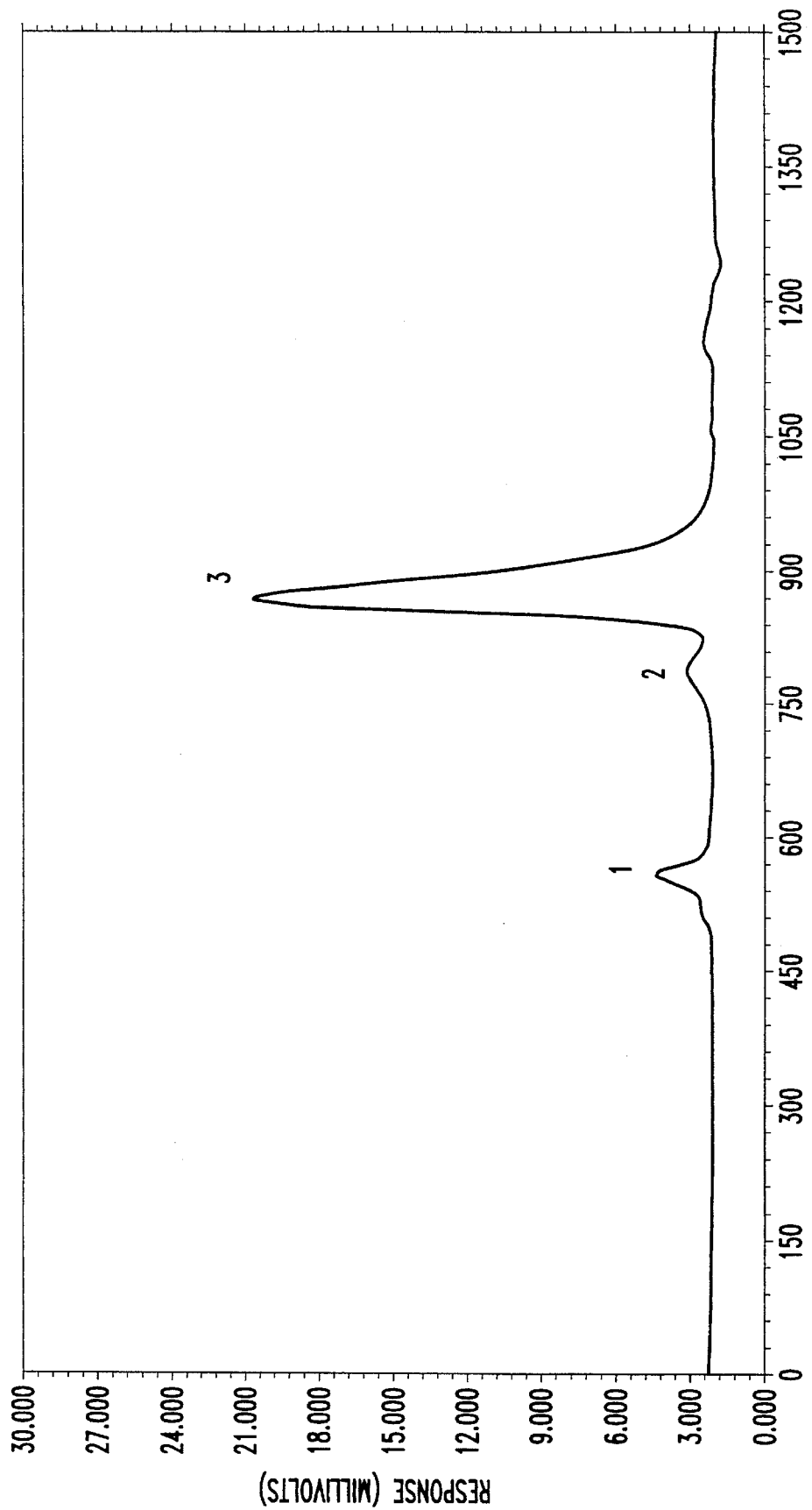
FIG. 9 is a size exclusion HPLC chromatogram of a bST bulk material using a borate/EDTA mobile phase having a pH of 7.3 as further described in the Example 2, infra., demonstrating the presence of the bST soluble aggregate (peak 1), dimer (peak 2) and monomer (peak 3).
Figure 10:
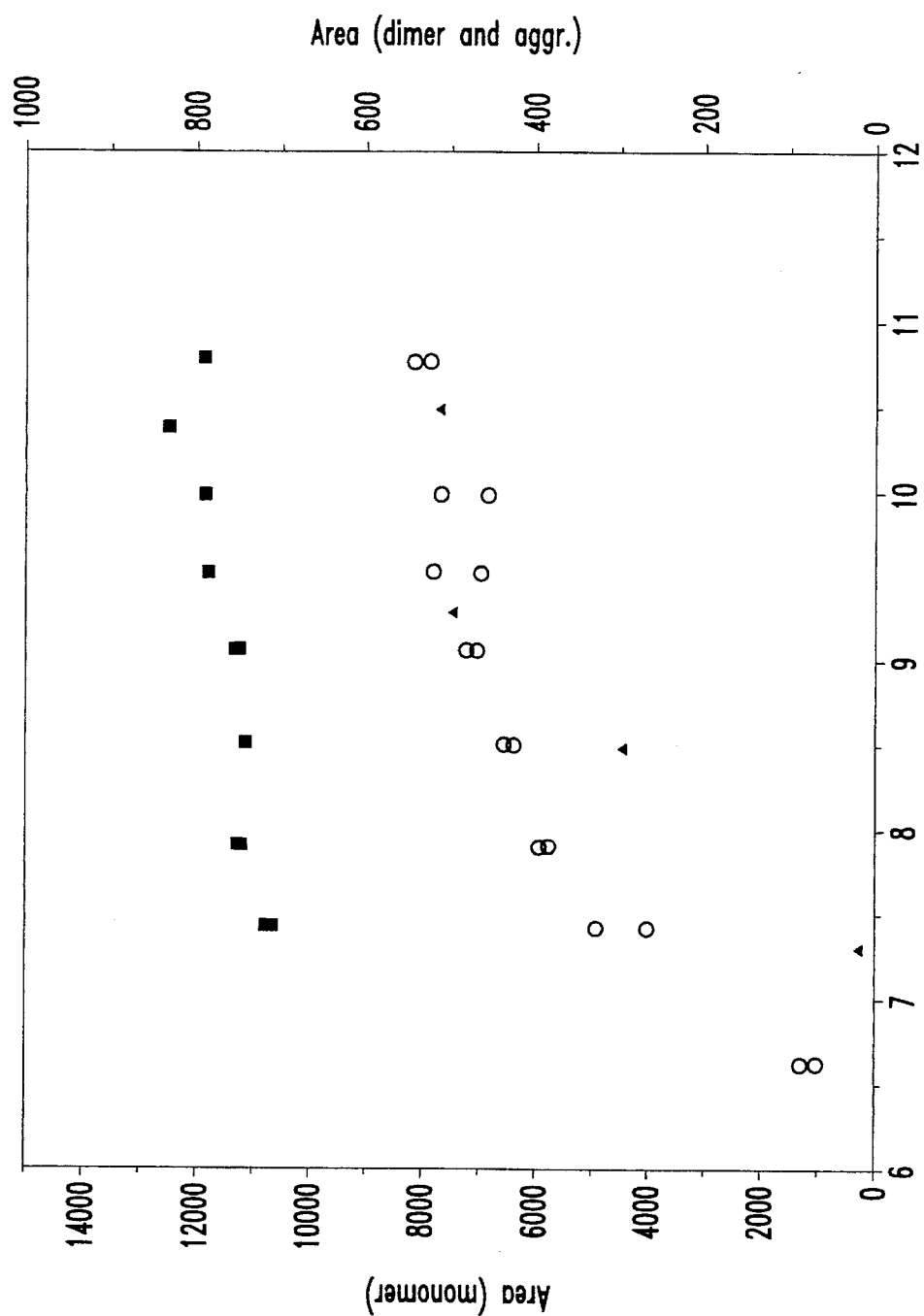
FIG. 10 is a graph showing the effect of borate mobile phase pH on the size exclusion HPLC peak area for the biologically active bST monomer fraction (■) and for the respective fractions including the dimer (○), bST soluble aggregate (Δ) under the conditions described in the Example 2, infra.

A typical SEC chromatogram obtained on the TSK G3000SW column is shown in FIG. 9. This column achieved reproducibility and chromatographic resolution in the separation of the three target species, rbST monomer, dimer and aggregates. In similar runs, a longer TSK G3000SW column, 7.5×600 mm, showed excellent resolution in the separation of rbST monomer and dimer but aggregates were lost due to decomposition resulting from the longer chromatographic process in the column.

pH effect in sample solutions pH effects on the solubility of rbST were studied. Results indicated that the rate of aggregation/precipitation increased with decreasing solution pH. In this study, we found that pH in the range of 6.7 to 11 in sodium borate/EDTA buffer solutions did not affect the elution time of the three targets in the HPSEC separation, but strongly affected the peak areas of dimer, and particularly, the aggregates. The pH-dependent peak areas of rbST monomer, dimer and aggregates are presented in FIG. 10. The peak areas of dimer and aggregates were not dependent on solution pH at pH greater than 9, but dramatically decreased with decreasing pH below 9. No dimer and aggregate peaks were found at pH below 7. At pH greater than 10.5, however, rbST monomer was not stable and more dimer resulted in solution. Therefore, the optimal condition for sample solution was pH 9.5 in sodium borate/EDTA buffer solution. In addition, the use of sodium borate/EDTA buffer with the same concentration as the mobile phase eliminates the influence of void peaks in the separation.

Mobile phase

Figure 11:
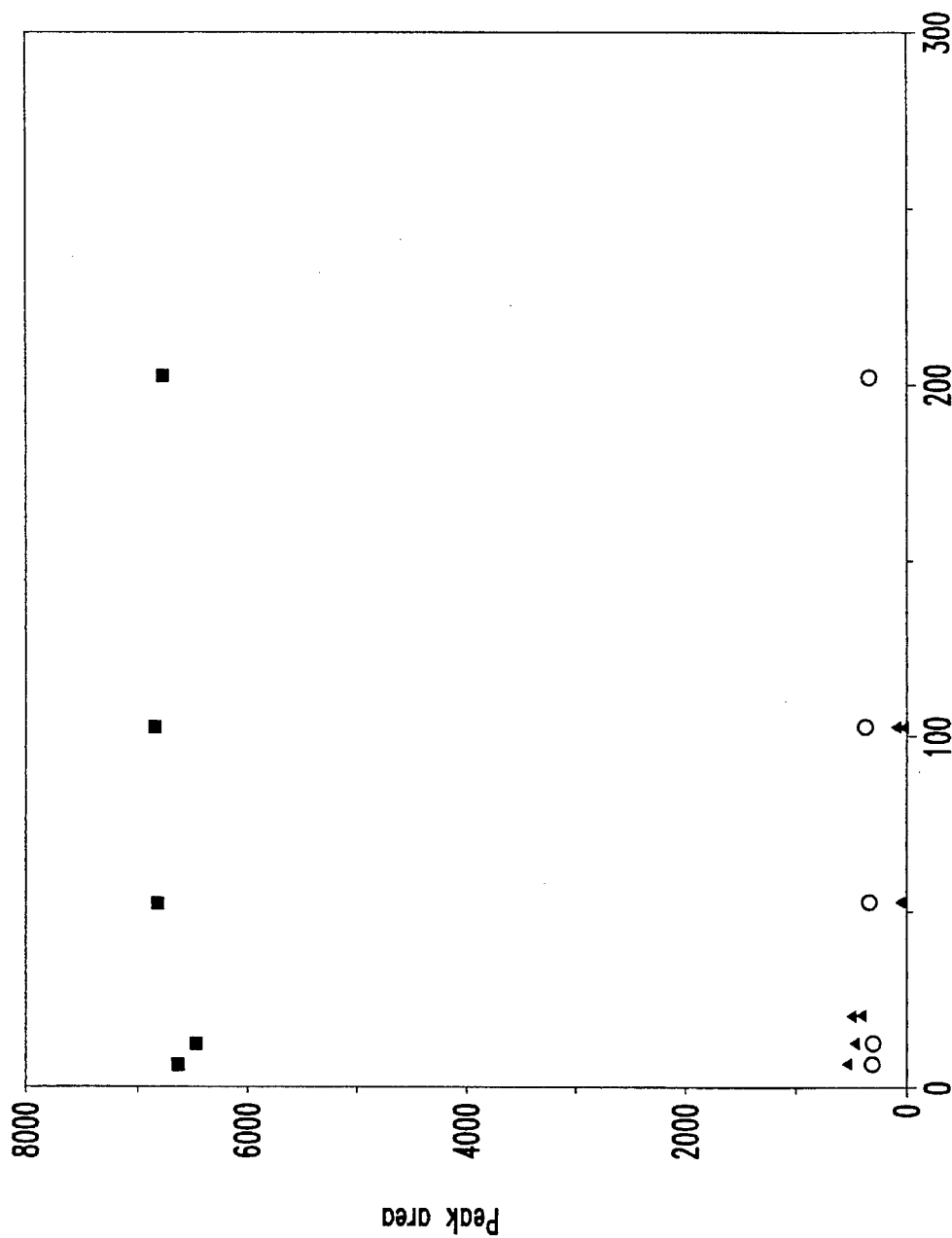
FIG. 11 is a graph showing the effect of borate concentration in pH 7.3 mobile phase on the size exclusion HPLC peak area for the biologically active bST monomer fraction (■) and for the respective fractions including the dimer (○), bST soluble aggregate (Δ) under the conditions described in the Example 2, infra.
Figure 12:
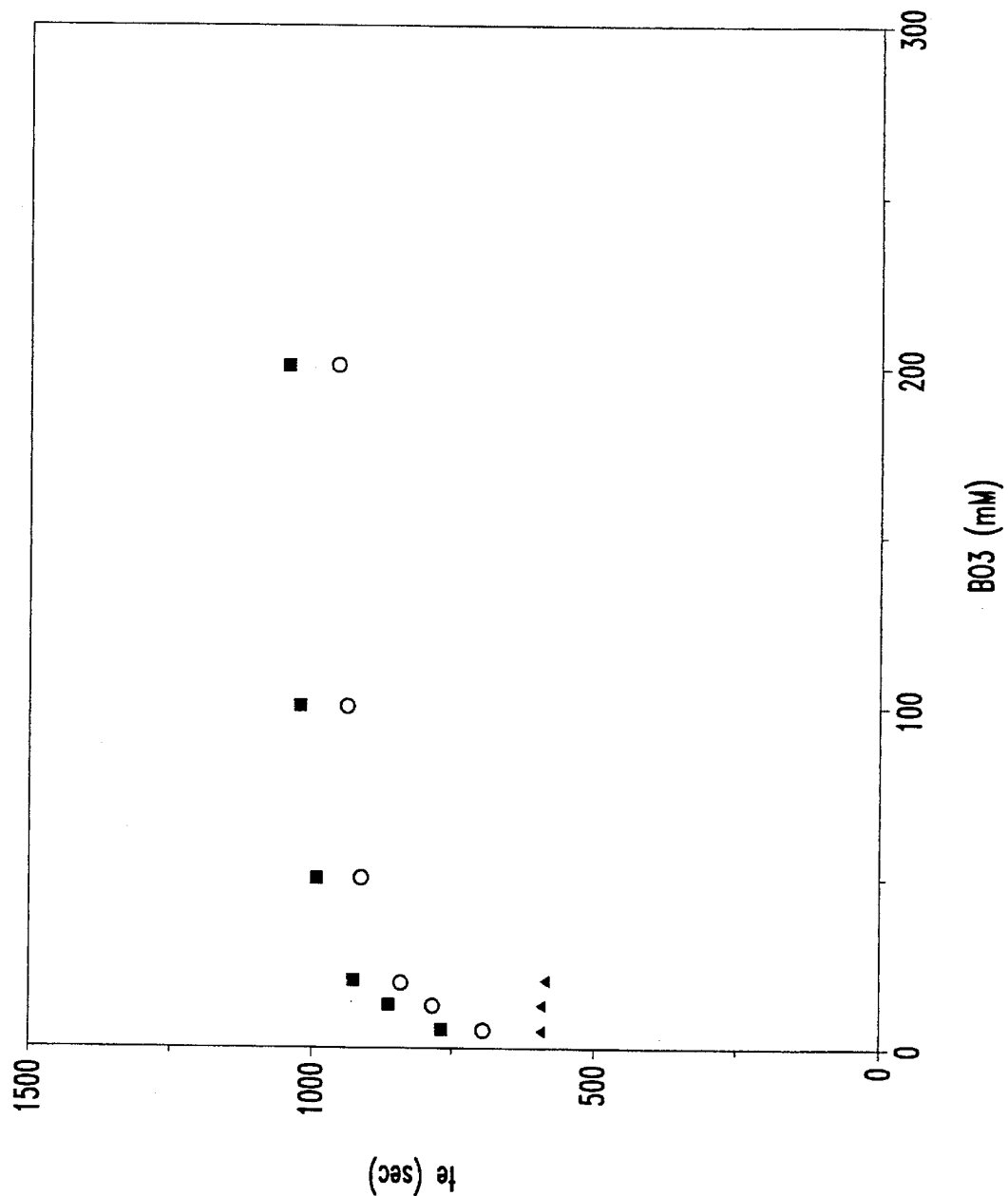
FIG. 12 is a graph showing the effect of borate concentration in the mobile phase on the size exclusion HPLC elution times for the biologically active bST monomer fraction (■) and for the respective fractions including the dimer (○), bST soluble aggregate (Δ) under the conditions described in the Example 2, infra.

In Example 1, it was shown that rbST aggregates were strongly affected by pH and buffer concentration in ammonium hydrogencarbonate solutions because of the strong hydrophobicity of aggregators. Aggregates can only be present in higher pH (greater than about 8.5) buffer solution. However, the silica based columns allowed pH less than 7.4 mobile phase to be used. In this study, a sodium borate—EDTA buffer at pH 7.3 was used in the separation and quantification of rbST and its oligomers. The pH of this buffer appears to be more stable than the ammonium hydrogencarbonate buffer. Consequently, rbST has excellent stability in this buffer solution. The effect of the buffer concentration in the mobile phase on peak areas of three target species is shown in FIG. 11. The results demonstrated that there was no significant effect of buffer concentration on peak areas of rbST monomer and dimer, but a strong effect was observed on the peak area of aggregates. When buffer concentration increased to 50 mM borate in the mobile phase, almost no aggregate peaks were found in the separation. Therefore, the soluble aggregates of rbST cannot be present in solutions with high buffer concentrations and low pH (see FIG. 10). The elution times of monomer and dimer increased with increasing buffer concentrations in the mobile phase (FIG. 12). A slight change in elution time of both the monomer and dimer was observed as the borate concentration increased to greater than 20 mM. The elution time of aggregates remained the same with increasing buffer concentration. EDTA present in the buffer solution enhances stability of rbST. On the basis of results obtained, 20 mM sodium borate—1.44 mM EDTA buffer solution at pH 7.3 was used as the mobile phase in this method.

Molecular mass measurements

Figure 13A:
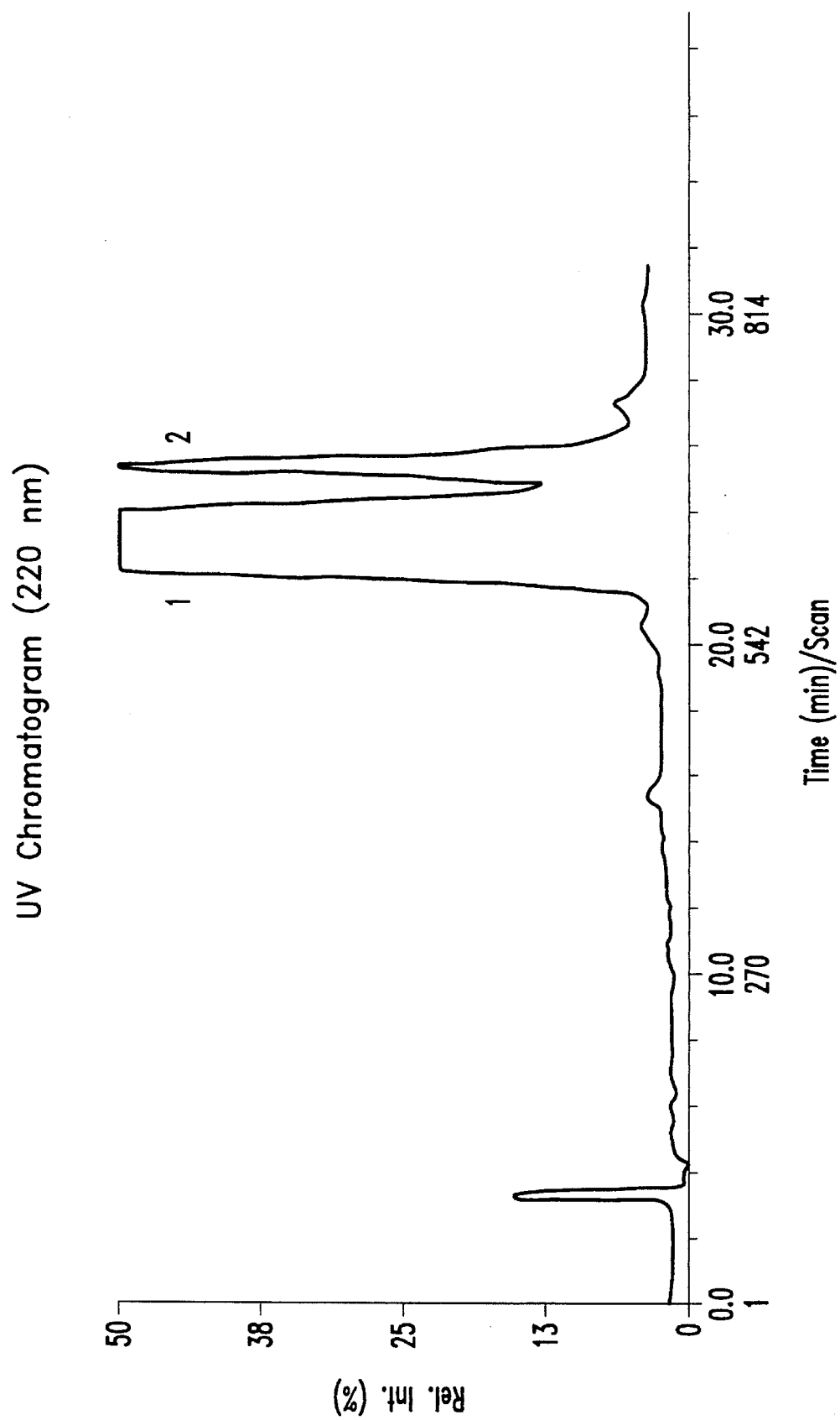
FIG. 13 provides reversed-phase HPLC-electrospray mass spectrum analyses confirming the apparent molecular masses of rbST monomer and dimer.
Figure 13B:
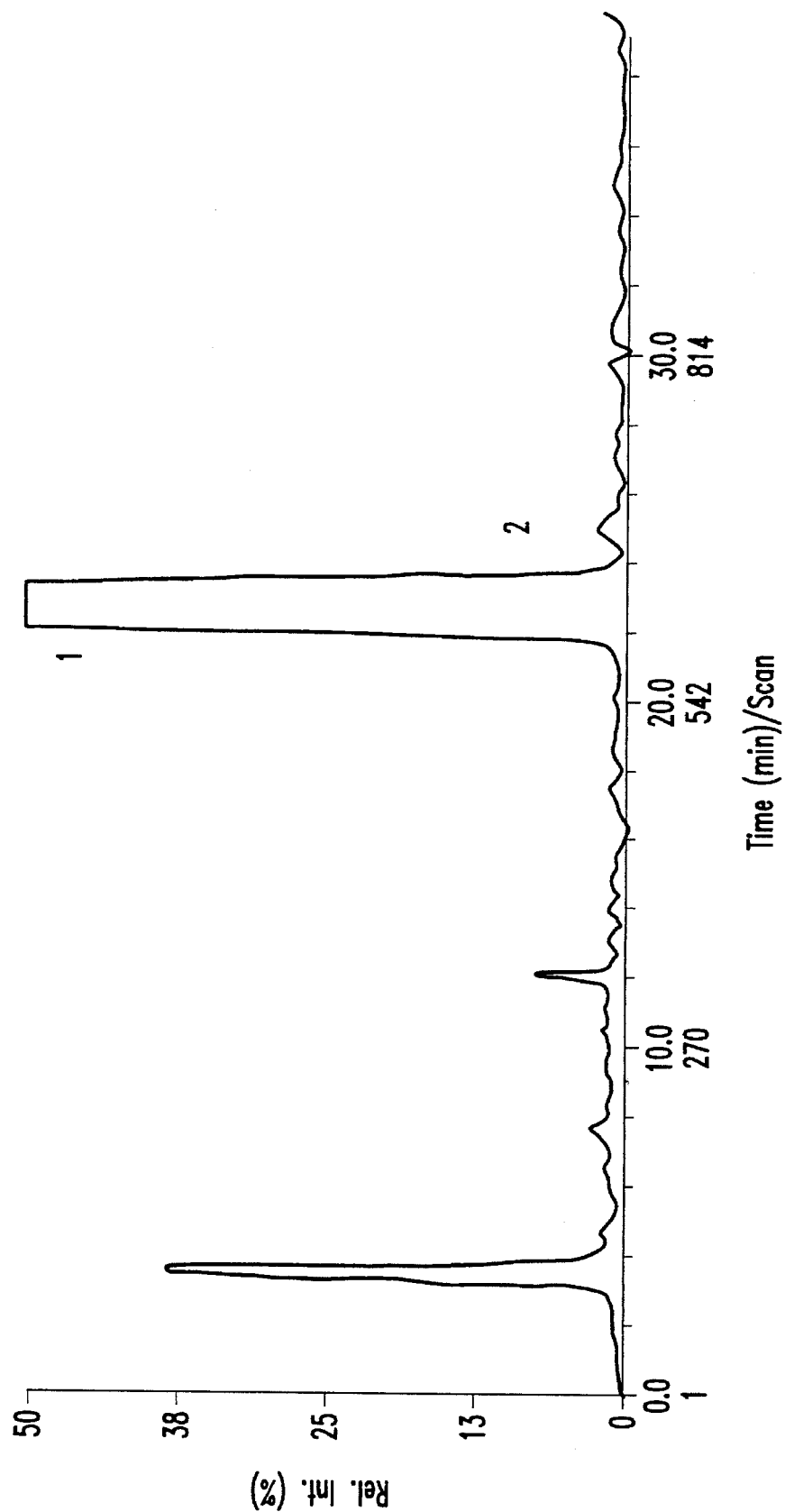
Figure 14A:
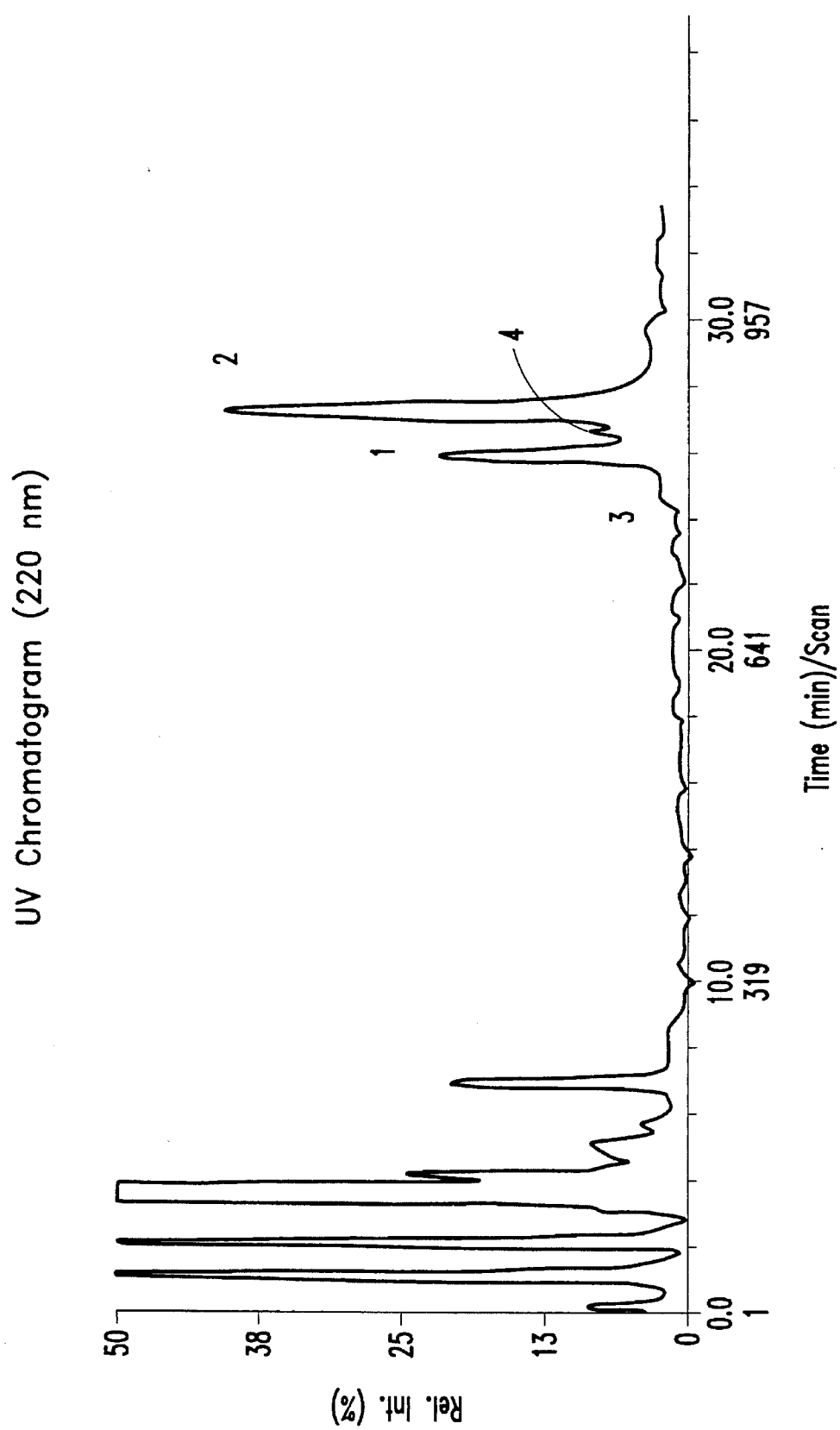
FIG. 14 provides provides reversed-phase HPLC-electrospray mass spectrum analyses of the rbST dimer.
Figure 14B:
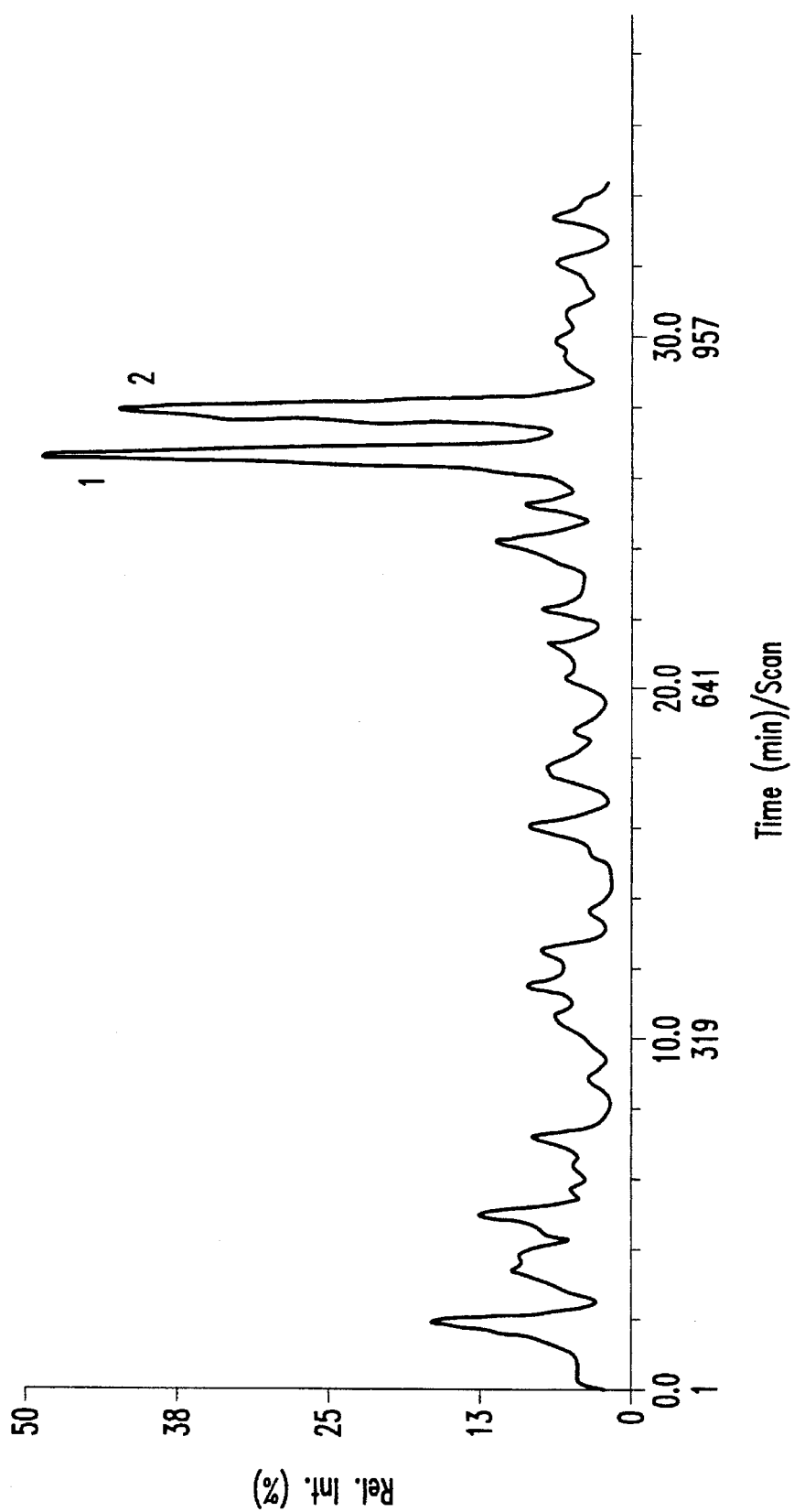

The apparent molecular masses of rbST monomer and dimer have been confirmed by using reversed phase HPLC-electrospray mass spectrum (LC-ESPMS). The results, shown in FIG. 13, revealed that the bulk drug substance contained two components in the TFA/ACN mobile phase as evidenced by the ultraviolet (UV) (FIG. 13A) and total ion chromatogram (TIC) (FIG. 13B). Mass spectral data associated with the peak 1 eluting at around 22.5 minutes indicated that this component was rbST monomer with a molecular mass of 22,819 daltons (calculated mass 22,818). The smaller peak 2 at a retention time of approximately 25 minutes was suspected rbST dimer. This component was found to exhibit a mass of 45,638 daltons by mass spectral data. No data were obtained for the molecular mass of rbST aggregates because they were dissociated by the strong acidic medium in the TFA/ACN mobile phase in the reversed phase HPLC. The isolated dimer component obtained by HPSEC is an enriched dimer mixture with the monomer. It provided further confirmatory evidence of the dimer identification. FIG. 14 shows comparative UV (FIG. 14A) and TIC (FIG. 14B) signal traces for this component. Spectral data obtained indicated that the first main peak represented rbST monomer with a mass of 22,819. The second main peak was confirmed to be the rbST dimer with a mass of 45,638.

Correlation between rat body weight gain assay and HPSEC assay

Figure 15:
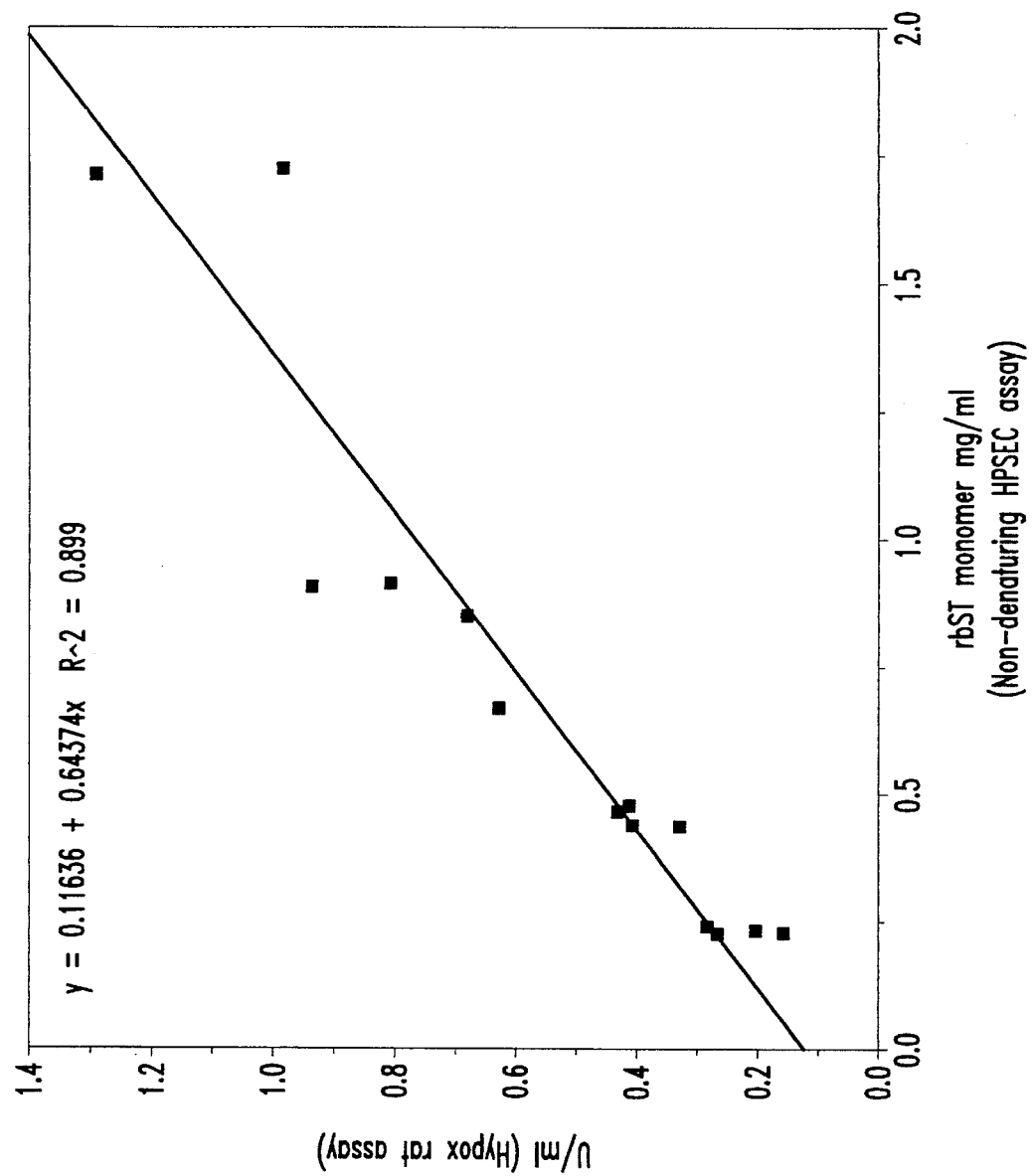
FIG. 15 is a graph showing the correlation between rat mass gain assay potency data (IU/mL) and the size exclusion HPLC-measured level of biologically active bST protein for bulk recombinant bST under the conditions described in the Example 2, infra.

The correlation between hypophysectomized rat body weight gain potency and HPSEC potency obtained by this method was investigated. Linear regression analysis of the data obtained by both assays using several lots of bulk drug substances is shown in FIG. 15. A regression coefficient of 0.899 was obtained. These results clearly demonstrate that the data obtained with this non-denaturing HPSEC method provide better precision and accuracy for rbST potency compared to hypophysectomized rat bioassay and it may be used to replace the hypophysectomized rat bioassay as a measure of potency assay for routine analysis.

Validation

The linearity of rbST monomer was evaluated by preparing different concentrations of rbST reference standard an the bulk drug substance from 0.05 to 2.0 mg/mL. A correlation coefficient of 0.999 was obtained for the monomer using linear regression analysis. The limit of quantification was 0.1 mg/mL.

Figure 16:
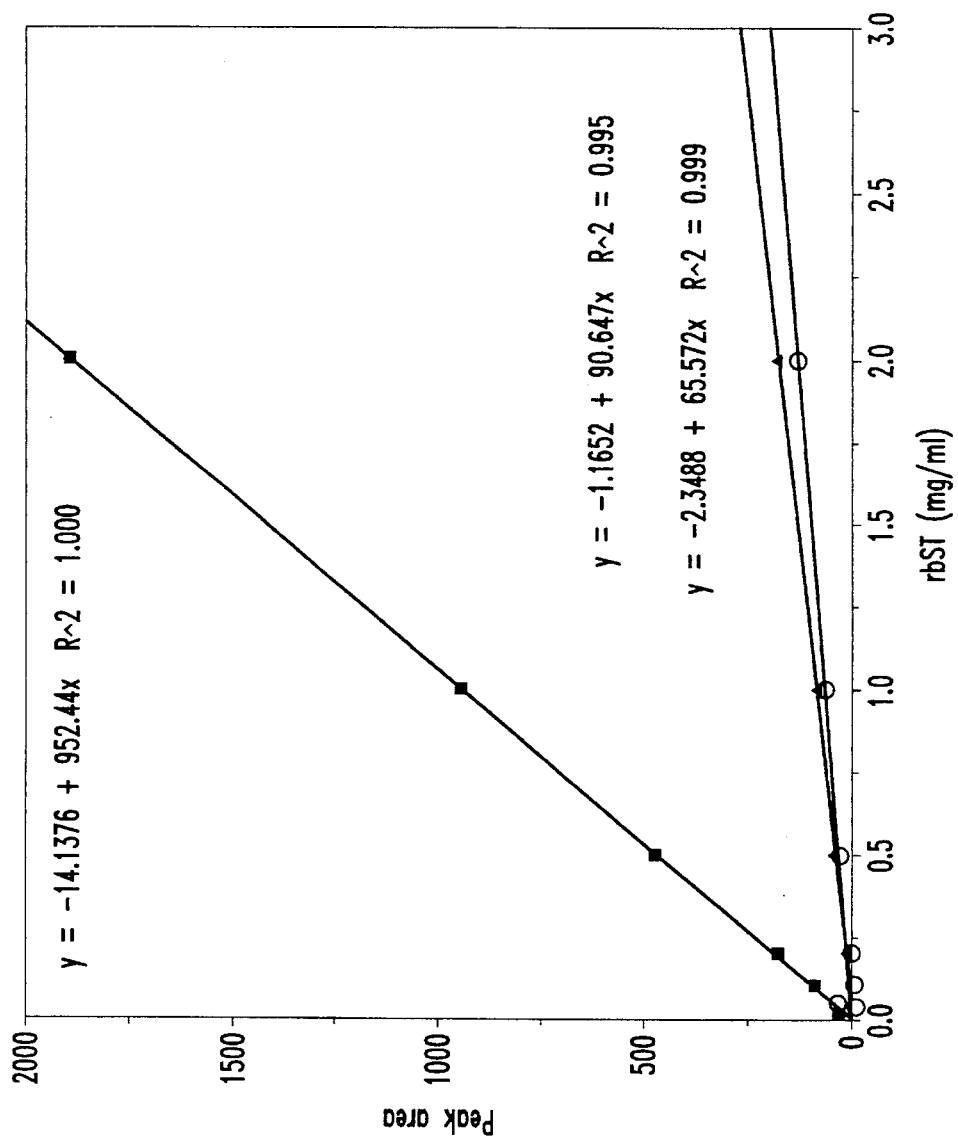
FIG. 16 is a graph of the size exclusion HPLC peak area versus solution concentration for the bST monomer (■), dimer (○) and soluble aggregate (Δ) under the conditions described in the Example 2, infra.

Owing to the difficulty of preparing the pure reference standard for both the dimer and aggregates, a normalization procedure with peak area ratio was employed to estimate rbST dimer and aggregates in bulk drug substances. The linearity of dimer and aggregates was evaluated by using solutions with varying concentration from 0.1 to 2.0 mg/mL (FIG. 16). The correlation coefficients were 0.999 for the lot containing 6 percent of dimer and 0.995 for the same lot containing 7 percent of aggregates. The limitation of estimation was 1 percent.

The precision of the method for determination of monomer and estimation of dimer and aggregates was assessed through triplicate analysis of three bulk samples for three different days. The results, shown in Table 4 (M=monomer; D=dimer; A=aggregate), indicate that the intra-day precision for monomer was 3 percent and inter-day precision within 3 days was 1.24 percent. The precision of dimer and aggregates in inter-day study were less than 6 percent RSD and about 20 percent RDS, respectively. Relatively lower precision in the estimation of soluble aggregates was due to low content (less than 1 percent) in the bulk drug substances.

TABLE 4

|  | Lot 4 | | | Lot 5 | | | Lot 6 | | |
| --- | --- | --- | --- | --- | --- | --- | --- | --- | --- |
|  | M % | D % | A % | M % | D % | A % | M % | D % | A % |
| Day 1 | 93.78 | 2.51 | 0.89 | 91.28 | 2.14 | 1.01 | 82.37 | 5.67 | 8.24 |
| RSD % (n = 3) | 2.10 | 8.0 | 14.0 | 0.45 | 11.9 | 23.4 | 1.34 | 3.5 | 3.4 |
| Day 2 | 92.77 | 2.54 | 0.63 | 91.94 | 2.27 | 0.79 | 81.21 | 5.48 | 8.70 |
| RSD % (n = 3) | 3.29 | 8.8 | 16.6 | 0.75 | 3.9 | 13.0 | 1.08 | 3.2 | 1.5 |
| Day 3 | 95.10 | 2.50 | 0.84 | 92.83 | 2.25 | 0.86 | 81.65 | 5.78 | 7.97 |
| RSD % (n = 5) | 1.35 | 8.7 | 21.4 | 0.84 | 6.6 | 12.30 | 1.11 | 1.9 | 1.6 |
| Day to Day | 93.88 | 2.52 | 0.79 | 92.01 | 2.22 | 0.89 | 81.65 | 5.64 | 8.30 |
| RSD % | 1.24 | 0.8 | 17.5 | 0.85 | 3.4 | 12.4 | 0.76 | 2.7 | 4.4 |

In order to assess the accuracy of this method, the solutions of two different lots were fortified with two different concentrations of standard solution. The average recovery was 94.0 percent (RSD percent=2.6).

The stability of rbST in pH 9.5 20 mM sodium borate—1.44 mM EDTA buffer solutions was evaluated at 2°–8° C. and room temperature over a period of two days by three lots of bulk drug substances. The variability was found to be 2.5 percent for the monomer in sodium borate EDTA solutions within two days. Degradation and oligomerization were found at pH greater than 10.5 buffer solution after 2 days.

While the invention has been illustrated and described in detail in the foregoing description, the same is to be considered as illustrative and not restrictive in character, it being understood that only the preferred embodiment has been described and that all changes and modifications that come within the spirit of the invention are desired to be protected.

What is claimed is:

1. A method for determining the potency of a bovine somatotropin sample, comprising:

providing a bovine somatotropin sample dissolved in a first aqueous buffer solution having a pH above 8.5 and less than 12 and which is non-denaturing to the bovine somatotropin sample, said aqueous buffer solution being effective for dissolving both biologically-active bovine somatotropin and biologically-inactive bovine somatotropin non-covalent aggregates having a molecular weight above about 500,000 daltons;

measuring the level of biologically-active bovine somatotropin in the bovine somatotropin sample by size exclusion HPLC employing as a mobile phase a second aqueous buffer solution which is non-denaturing to the bovine somatotropin sample; said size exclusion HPLC also employing a stationary phase which is stable against degradation at the pH of said mobile phase; and determining the potency of the bovine somatotropin sample based upon the measured level of biologically active bovine somatotropin in the sample.

2. The method of claim 1 wherein:

said stationary phase is comprised of a hydrophilic porous silica gel, and wherein said mobile phase is a buffered aqueous solution having a pH in the range of about 7 to about 8.

3. The method of claim 1 wherein said first and second buffered aqueous solutions are essentially the same in composition.

4. The method of claim 1 wherein said hydrophilic porous polymer gel has an average particle size of about 10 μm to about 15 μm.

5. The method of claim 1 wherein:

said stationary phase is comprised of a hydrophilic porous polymer gel.

6. The method of claim 5 wherein:

said second buffered aqueous solution has a pH in the range of about 8.5 to about 12.

7. The method of claim 1 wherein said first buffered aqueous solution has a pH higher than that of the second buffered aqueous solution.

8. The method of claim 7 wherein said second buffered aqueous solution has a pH of about 7 to less than 8.

9. The method of claim 1 wherein said hydrophilic porous gel has an average particle size of about 10 μm.

10. The method of claim 9 wherein said hydrophilic porous gel has an average pore diameter of about 150 angstroms.

11. The method of claim 9 wherein said size exclusion HPLC is conducted at a pressure of about 800 to about 1000 psi.

12. The method of claim 1 wherein said first and second buffered aqueous solutions are selected from the group consisting of a bicarbonate buffer solution and a borate buffer solution.

13. The method of claim 12 wherein said first and second buffered aqueous solutions are borate buffer solutions.

14. The method of claim 13 wherein said borate buffer solutions have a borate ion concentration of less than about 0.05M.

15. The method of claim 14 wherein said first buffered aqueous solution is a borate buffer solution having a pH above 9, and said second buffered aqueous solution is a borate buffer solution having a pH in the range of 7 to 8.

16. The method of claim 15 wherein said first and second buffered aqueous solutions also comprise EDTA.

17. The method of claim 15 wherein said first buffered aqueous solution is a borate buffer solution having a pH in the range of 9 to 10, and said second buffered aqueous solution is a borate buffer solution having a pH in the range of 7 to 7.5.

18. The method of claim 17 wherein said hydrophilic porous gel has an average particle size of about 10 μm to about 15 μm.

19. A method for chromatographically treating somatotropin, comprising:

providing a somatotropin sample dissolved in a first aqueous buffer solution having a pH above 8.5 and less than 12 said first aqueous buffer solution being effective for dissolving both biologically-active somatotropin and biologically-inactive somatotropin non-covalent aggregates having a molecular weight above about 500,000 daltons; and measuring the level of somatotropin monomer in said dissolved sample, said measuring including subjecting the somatotropin sample to size exclusion HPLC employing as a stationary phase a hydrophilic porous gel having an average particle diameter of about 5 μm to about 15 μm and as a mobile phase a second aqueous buffer solution having a pH in the range of 7 to 8 and which is non-denaturing to the somatotropin sample.

20. The method of claim 19, wherein said somatotropin sample comprises biologically active somatotropin and biologically inactive somatotropin non-covalent aggregates having a molecular weight above about 500,000 daltons.

21. The method of claim 20 wherein said stationary phase is comprised of a hydrophilic porous silica gel.

22. The method of claim 21 wherein said stationary phase is comprised of a hydrophilic porous polymer gel.

23. The method of claim 19 wherein said first buffered aqueous solution has a pH above 9.

24. The method of claim 23 wherein said second buffered aqueous solution has a pH in the range of 7 to 7.5.

25. The method of claim 24 wherein said first and second buffered aqueous solutions are selected from the group consisting of borate buffers solutions and bicarbonate buffer solutions.

26. The method of claim 25 wherein said first and second buffer solutions are borate buffer solutions having a borate ion concentration of less than 0.05M.

27. The method of claim 26 wherein said first and second buffer solutions further comprise EDTA.

28. The method of claim 27 wherein said first and second buffer solutions have a borate ion concentration of about 0.02M or less.

29. The method of claim 28 wherein said somatotropin is selected from the group bovine somatotropin, porcine somatotropin and human somatotropin.

30. The method of claim 29 wherein said somatotropin is bovine somatotropin.

31. A method for chromatographically treating bulk recombinant somatotropin, comprising:

preparing a sample by reconstituting the somatotropin in a first aqueous borate buffer solution having a pH above 9 and less than 11, said first aqueous borate buffer solution being non-denaturing to the somatotropin and having a borate ion concentration of less that about 0.05M so as to be effective for dissolving any somatotropin occurring in the form of non-covalent somatotropin soluble aggregates with molecular weights above about 500,000 daltons; and measuring the level of somatotropin monomer in the sample by size exclusion HPLC employing as a stationary phase a hydrophilic porous gel having an average particle diameter of about 5 μm to about 15 μm and as a mobile phase a second aqueous borate buffer solution having a pH in the range of 7 to 8, said second borate buffer solution also being non-denaturing to the somatotropin sample and having a borate ion concentration of less than about 0.05M.

32. The method of claim 31, wherein said first and second aqueous borate buffer solutions also comprise EDTA.

33. The method of claim 32, wherein said first aqueous borate buffer solution has a pH in the range of 9 to 10.

34. The method of claim 33, wherein said somatotropin is selected from the group bovine somatotropin, porcine somatotropin and human somatotropin.

35. The method of claim 34, wherein said somatotropin is bovine somatotropin.

* * * * *